US012765543B2

(12) United States Patent
Gandhi et al.

(10) Patent No.: US 12,765,543 B2
(45) **Date of Patent: *Oct. 20, 2026**

(54) ANTIMICROBIAL COMPOSITIONS AND RELATED METHODS OF USE

(71) Applicant: Jeneil Biosurfactant Company, LLC, Saukville, WI (US)

(72) Inventors: Niranjan R. Gandhi, River Hills, WI (US); Victoria Palmer Skebba, Cedarburg, WI (US); Gary A. Strobel, Bozeman, MT (US)

(73) Assignee: Jeneil Biosurfactant Company, LLC, Saukville, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/165,814

(22) Filed: Feb. 7, 2023

(65) Prior Publication Data

US 2023/0172199 A1 Jun. 8, 2023

Related U.S. Application Data

(60) Continuation of application No. 16/416,933, filed on May 20, 2019, now Pat. No. 11,570,986, which is a continuation of application No. 15/651,824, filed on Jul. 17, 2017, now Pat. No. 10,292,386, which is a division of application No. 13/815,839, filed on Mar. 15, 2013, now Pat. No. 9,706,773, which is a continuation-in-part of application No. 12/768,529, filed on Apr. 27, 2010, now Pat. No. 8,728,462.

(60) Provisional application No. 61/315,611, filed on Mar. 19, 2010, provisional application No. 61/257,319, filed on Nov. 2, 2009, provisional application No. 61/214,752, filed on Apr. 27, 2009.

(51) Int. Cl.

| | |
|---|---|
| ***A01N 31/02*** | (2006.01) |
| ***A01N 25/08*** | (2006.01) |
| ***A01N 25/34*** | (2006.01) |
| ***A01N 35/02*** | (2006.01) |
| ***A01N 35/04*** | (2006.01) |
| ***A01N 37/02*** | (2006.01) |
| ***A01N 37/06*** | (2006.01) |
| ***A23B 2/754*** | (2025.01) |
| ***A23B 2/758*** | (2025.01) |
| ***A23B 2/779*** | (2025.01) |
| ***A23B 4/20*** | (2006.01) |
| ***A23B 7/154*** | (2006.01) |
| ***A61K 45/06*** | (2006.01) |

(52) U.S. Cl.

CPC ............. *A01N 31/02* (2013.01); *A01N 25/08* (2013.01); *A01N 25/34* (2013.01); *A01N 35/02* (2013.01); *A01N 35/04* (2013.01); *A01N 37/02* (2013.01); *A01N 37/06* (2013.01); *A23B 2/754* (2025.01); *A23B 2/758* (2025.01); *A23B 2/779* (2025.01); *A23B 4/20* (2013.01); *A23B 7/154* (2013.01); *A61K 45/06* (2013.01)

(58) Field of Classification Search

None

See application file for complete search history.

(56) References Cited

U.S. PATENT DOCUMENTS

| | | | |
|---|---|---|---|
| 2,711,976 | A | 6/1955 | Castellani |
| 2,866,819 | A | 12/1958 | Montangna |
| 2,910,368 | A | 10/1959 | Melnick et al. |
| 3,119,691 | A | 1/1964 | Ludington et al. |
| 3,806,600 | A | 4/1974 | Lapore et al. |
| 3,947,570 | A | 3/1976 | Pensak et al. |
| 4,349,459 | A | 9/1982 | Romero-Sierra et al. |
| 4,356,204 | A | 10/1982 | Robach |
| 4,500,517 | A | 2/1985 | Luss |
| 4,548,808 | A | 10/1985 | Chavkin |
| 4,575,891 | A | 3/1986 | Valente |
| 4,581,238 | A | 4/1986 | White et al. |
| 4,721,059 | A | 1/1988 | Lowe et al. |
| 4,988,576 | A | 1/1991 | Lin et al. |
| 5,060,598 | A | 10/1991 | Richards |
| 5,176,903 | A | 1/1993 | Goldberg et al. |
| 5,273,769 | A | 12/1993 | Lajoie et al. |
| 5,455,232 | A | 10/1995 | Piljac et al. |
| 5,547,987 | A | 8/1996 | Bland et al. |
| 5,670,475 | A | 9/1997 | Trinh et al. |
| 5,767,090 | A | 6/1998 | Stanghellini et al. |
| 5,783,544 | A | 7/1998 | Trinh et al. |
| 5,807,587 | A | 9/1998 | Cox et al. |

(Continued)

FOREIGN PATENT DOCUMENTS

| | | |
|---|---|---|
| CA | 1159271 A | 12/1983 |
| CA | 2760150 A1 | 11/2010 |

(Continued)

OTHER PUBLICATIONS

Wilson, C. et al., "Benzaldehyde as a Soil Fumigant, and an Apparatus for Rapid Fumigant Evaluation", Horticulture Science, vol. 34(4), pp. 681-685. (Year: 1999).*

(Continued)

*Primary Examiner* — Grant C Currens

(74) *Attorney, Agent, or Firm* — Reinhart Boerner Van Deuren s.c.

(57) ABSTRACT

Antimicrobial compositions comprising one or more compound components generally recognized as safe for human consumption, and related methods of use, such compositions and methods as can be employed in a wide range of agricultural, industrial, building, pharmaceutical and/or personal care products and applications.

14 Claims, 11 Drawing Sheets

(56) References Cited

U.S. PATENT DOCUMENTS

| | | | | |
|---|---|---|---|---|
| 5,866,182 | A | 2/1999 | Exner et al. | |
| 5,968,207 | A | 10/1999 | Li | |
| 6,156,362 | A | 12/2000 | Cirigliano et al. | |
| 6,187,327 | B1 | 2/2001 | Stack | |
| 6,231,840 | B1 | 5/2001 | Buck | |
| 6,231,845 | B1 | 5/2001 | Morissey et al. | |
| 6,250,511 | B1 | 6/2001 | Kelly | |
| 6,287,550 | B1 | 9/2001 | Trinh et al. | |
| 6,403,063 | B1 | 6/2002 | Sawyer | |
| 6,566,349 | B1 | 5/2003 | Anderson et al. | |
| 6,699,825 | B2 | 3/2004 | Rees et al. | |
| 6,720,450 | B2 | 4/2004 | Linderman | |
| 6,812,217 | B2 | 11/2004 | Hendriks | |
| 6,911,338 | B2 | 6/2005 | Strobel et al. | |
| 6,960,350 | B2 | 11/2005 | Hanada et al. | |
| 7,070,985 | B2 | 7/2006 | Strobel et al. | |
| 7,163,708 | B2 | 1/2007 | Dalziel et al. | |
| 7,192,575 | B2 | 3/2007 | Ryan et al. | |
| 7,267,975 | B2 | 9/2007 | Strobel et al. | |
| RE40,050 | E | 2/2008 | Coughlin et al. | |
| 7,341,862 | B2 | 3/2008 | Strobel et al. | |
| 7,449,130 | B2 | 11/2008 | Lloyd et al. | |
| 7,498,050 | B2 | 3/2009 | Kincaid et al. | |
| 7,507,429 | B2 | 3/2009 | Man et al. | |
| 7,575,744 | B2 | 8/2009 | Doyle et al. | |
| 7,659,326 | B2 | 2/2010 | McCarthy | |
| 7,863,350 | B2 | 1/2011 | Brander et al. | |
| 7,943,565 | B2 | 5/2011 | Kany et al. | |
| 7,968,499 | B2 | 6/2011 | Gandhi | |
| 7,985,722 | B2 | 7/2011 | Desanto | |
| 7,998,278 | B2 | 8/2011 | Hackenberger et al. | |
| 8,188,025 | B2 | 5/2012 | Kany et al. | |
| 8,728,442 | B2 | 5/2014 | Jimenez et al. | |
| 2002/0098159 | A1 | 7/2002 | Wei et al. | |
| 2004/0141955 | A1 | 7/2004 | Strobel et al. | |
| 2004/0206697 | A1 | 10/2004 | Strobel et al. | |
| 2006/0003057 | A1 | 1/2006 | Kelly et al. | |
| 2006/0127347 | A1 | 6/2006 | Strobel et al. | |
| 2006/0243212 | A1 | 11/2006 | Jenkins et al. | |
| 2007/0087094 | A1 | 4/2007 | Schuer | |
| 2007/0166440 | A1 * | 7/2007 | Davie | A23B 7/16 426/323 |
| 2007/0191292 | A1 | 8/2007 | Gandhi et al. | |
| 2008/0213194 | A1 | 9/2008 | DeSanto | |
| 2010/0272690 | A1 | 10/2010 | Gandhi et al. | |
| 2012/0058058 | A1 | 3/2012 | Jimenez et al. | |
| 2013/0302480 | A1 | 11/2013 | Gandhi et al. | |

FOREIGN PATENT DOCUMENTS

| | | | |
|---|---|---|---|
| CN | 1845676 | A | 10/2006 |
| CN | 102409323 | A | 4/2012 |
| CN | 102458129 | A | 5/2012 |
| EP | 1964543 | A1 | 9/2008 |
| EP | 1666377 | B1 | 2/2009 |
| EP | 1379126 | | 10/2009 |
| JP | 2004513153 | A | 4/2004 |
| JP | 2004321147 | A | 11/2004 |
| JP | 2012525394 | A | 10/2012 |
| KR | 1020120047847 | A | 5/2012 |
| KR | 20130016779 | A | 2/2013 |
| WO | 199943334 | A1 | 9/1999 |
| WO | 2005009360 | | 2/2005 |
| WO | 2010129285 | A2 | 11/2010 |
| WO | 2010130028 | A1 | 11/2010 |
| WO | 2012158448 | A2 | 11/2012 |
| WO | 2013059012 | A1 | 4/2013 |
| WO | 2013081777 | A1 | 6/2013 |

OTHER PUBLICATIONS

Sarkar et al., "Incidence of post-harvest fungal diseases of banana fruit in Warangal market", Indian Phytopathology, vol. 62(1), pp. 103-105. (Year: 2009).*

Ouattara et al., "Inhibition of surface spoilage bacteria in processed meats by application of antimicrobial films prepared with chitosan", International Journal of Food Microbiology, vol. 62, pp. 139-148 (Year: 2000).*

Cagri et al., "Antimicrobial Edible Films and Coatings", Journal of Food Protection, vol. 67, No. 4, pp. 833-848. (Year: 2004).*

Utama et al., "In Vitro Efficacy of Plant Volatiles for Inhibiting the Growth of Fruit and Vegetable Decay Microorganisms", Journal of Agricultural and Food Chemistry, vol. 50, pp. 6371-6377. (Year: 2002).*

Nagaoka et al., "Antimicrobial Activity of Sodium Citrate Against *Streptococcus pneumoniae* and Several Oral Bacteria", Letters in Applied Microbiology, 51, 546-551, 2010.

Maruzzella, J.C., et al., "Effects of Vapors of Aromatic Chemicals on Fungi", Journal of Pharmaceutical Sciences, vol. 50, 8, 665-668, 1960.

Bail, S., et al., "Antimicrobial Activities of Roman Chamomile Oil from France and Its Main Compounds", Journal of Essential Oil Research, vol. 21, 283-286, 2009.

Woolford, M.K., "The antimicrobial spectra of organic compounds with respect to their potential as hay preservatives", Crass and Forage Science, vol. 39, 75-79, 1984.

Friedman, M. et al., "Antibacterial Activities of Phenolic Benzaldehydes and Benzoic Acids against Campylobacter ejuni, *Escherichia coli*, Listeria monocytogenes, and *Salmonella enterica*", J Food Prot, 66(10), 2003, 1811-1821.

Hamdy M. Abdel-Rahman et al., "Synthesis of [beta]-hydroxypropanoic Acid Derivatives as Potential Anti-Inflammatory, Analgesic and Antimicrobial Agents", Arch. Pharm. Life Sci., 339, 2006, 378-387.

Priyanka Kudalkar et al., "Muscodor sutura, a novel endophytic fungus with volatile antibiotic activities", Mycoscience, (2012) 53:319-325.

M.G. Paulraj et al., "Toxicity of Benzaldehyde and Propionic Acid against Immature and Adult Stages of Aedes aegypti and Culex quinquefasciatus", J. Entomol., 8 (6): 539-547, 2011.

European Search Report for 14765584.9 dated Sep. 27, 2016, 27 pages.

B Ouattara et al., "Diffusion of Acetic and Propionic Acids from Chitosan-based Antimicrobial Packaging Films", Journal of Food Science, 2000, 65, 768-773.

S. Quintavalla et al., "Antimicrobial food packaging in meat industry Experimental Station for the Food Preserving Industry", Meat Science, 62, 2002, 373-380.

D.S. Chu et al., "Biopolymer-based antimicrobial packaging: a review", CRC Critical Reviews in Food Science and Nutrition, vol. 44, No. 4, 2004, 223-237.

European Opinion: "Scientific Opinion on the safety and efficacy of propionic acid, sodium propionate, calcium propionate and ammonium propionate for all animal species", the EFSA Journal, vol. 9, No. 12, 2011.

Supplementary Partial European Search Report for 14 765584.9 dated Jun. 28, 2016, 9 pages.

Morath, S. et al., "Fungal volatile organic compounds: A review with emphasis on their biotechnological potential", Fungal Biology Reviews, 2012, vol. 26, 73-83.

PCT International Search Report and Written Opinion from International Application No. PCT/2014/030657, Jul. 17, 2014, 14 pages.

Mitchell, A.M. et al., "Volatile antimicrobials from Muscodor crispans, a novel endophytic fungus," Microbiology, vol. 156, No. 1, Jan. 1, 2010, pp. 270-277.

Prange, Robert K. et al., "Perspectives on postharvest biopesticides and storage technologies for organic product", HortScience, vol. 41 (2), Apr. 1, 206, pp. 301-303.

Supplementary European Search Report, Apr. 24, 2013.

Stinson et al., "An endophytic *Gliocladium* sp. of Eucryphia cordifolia producing selective volatile antimicrobial compounds", Plant Science 165 (2003) 913-922.

Atmosukarto I, et al., "Isolation and characterization of Muscodor albus 1-41.3s, a volatile antibiotic producing fungus", Plant science 169 (2005) 854-861.

(56) References Cited

OTHER PUBLICATIONS

Strobel, GA, et al., “Volatile antimicrobials from Muscodor albus, a novel endophytic fungus”, Microbiology (2001), 147, 2943-2950.
Mitchell, A.M. et al., “Muscodor Crispans, A Novel Endophyte from Ananassoides in the Bolivian Amazon,” Fungal Diversity, 2008, vol. 31, pp. 37-43. See Abstract; fig. 1-3.
Ezra, D. et al., “New Endophytic Isolates of Muscodor Albus, a Volatile-Antibiotic-Producing Fungus, ” Microbiology, 2004, vol. 150, pp. 4023-4031. See Abstract; examples 1-6; tables 1 & 2.
Strobel, G., “Harnessing Endophytes for Industrial Microbiology,” Current Opinion in Microbiology, 2006, vol. 9, pp. 240-244. See Abstract; fig. 1.
Ezra, D. et al., “Effect of Substrate on the Bioactivity of Volatile Antimicrobials Produced by Muscodor Albus,” Plant Science, 2003, vol. 165, pp. 1229-1238. See Abstract; tables 1-6.
Mitchell, A.M. et al., “Volatile Antimicrobials from Muscodor crispans, a Novel Endophytic Fungus”, Microbiology, vol. 156, No. 1, Jan. 1, 2010, pp. 301-303.
1-Butanol, 3-methyl-, acetate. material measurement laboratory. NIST. 2011. p. 1-2.
Propionic acid. Information sheet from Technical Evaluation Report for the USDA National Organic Program. Sep. 3, 2008. p. 1-7.
Final Report on the Safety Assessment of Benzaldehyde. International Journal ofToxicology. 25(Suppl. 1 ): 11-27, 2006.
Sauceda, E.N.R., Use of Natural Antimicrobial Agents in the Preservation of Fruits and Vegetables, Ra Ximhai vol. 7, No. 2, Jan.-Apr. 2011.
Mani-Lopez, E. et al., “Organic Acids as Antimicrobials to Control Salmonella in Meat and Poultry Products”, Food Research International, vol. 45, No. 2, Mar. 1, 2012, pp. 713-721.
Irie et al., “Pseudomonas aeruginosa rhamnolipids disperse Bordetella bronchiseptica biofilms”, FEMS Microbiology Letters, vol. 250, pp. 237-243, 2005.
McDonnell et al., “Antiseptics and Disinfectants: Activity, Action, and Resistance”, Clinical Microbiology Reviews, vol. 12, No. 1, pp. 147-179 (1999).
Lens et al., “Antimicrobial activity of Butyl acetate, Ethyl acetate and Isopropyl alcohol on undesirable microorganisms in cosmetic products”, International Journal of Cosmetic Science, vol. 38, pp. 476-480 (2016).

* cited by examiner $R_1$ = H, OH, alpha-L-rhamnopyranosyl;

$R_2$ = H, $-CH(R_4)-CH_2-COOH$;

$R_3$ =($C_5$-$C_{20}$)-saturated, -mono- of poly-unsaturated alkyl;

$R_4$ =($C_5$-$C_{20}$)-saturated, -mono- of poly-unsaturated alkyl.

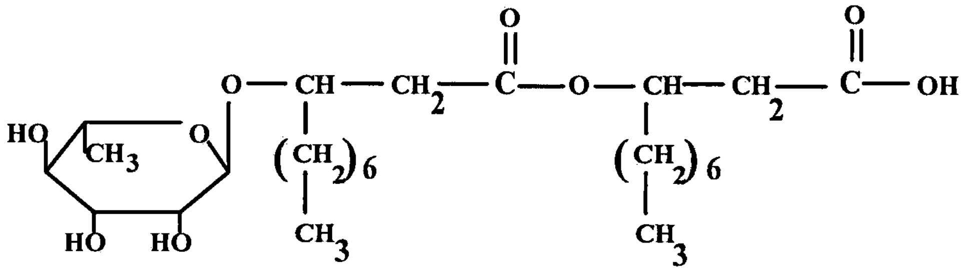
R1 -- α - L - RHAMNOPYRANOSYL - β- HYDROXYDECANOYL - β - HYDROXYDECANOATE
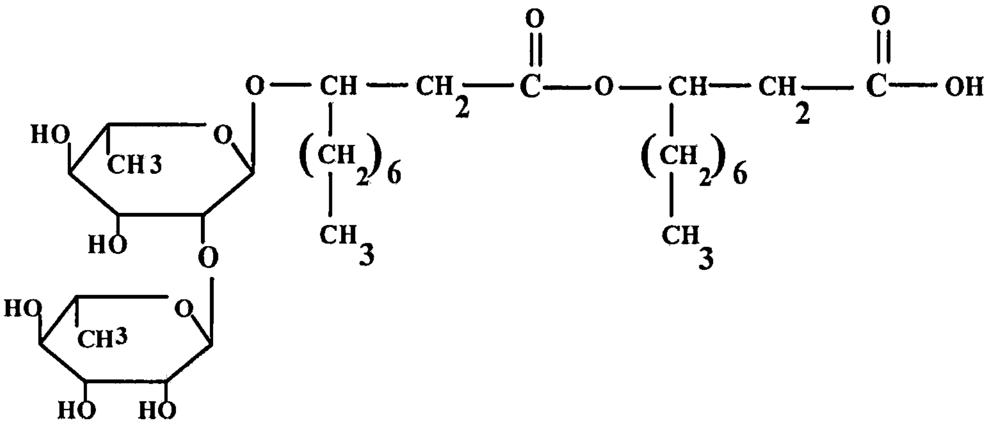
R2 -- 2-O-α-L-RHAMNOPYRANOSYL-α-L- RHAMNOPYRANOSYL - β-HYDROXYDECANOYL- β-HYDROXYDECANOATE
Fig. 9

Figure 10

| | | |
|---|---|---|
| Common Name<br>(Chemical Abstracts) | Structure | IUPAC Name* |
| Propanoic acid | 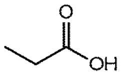 | Propionic acid |
| Isoamyl acetate<br><br>(Acetic acid, 3-methylbutyl ester) | 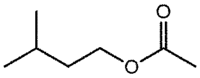 | Isopentyl acetate |
| Isobutyl isobutyrate<br><br>(Propanoic acid, 2-methyl-, 2-methylpropyl ester) | 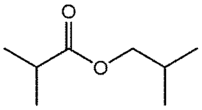 | Isobutyl isobutyrate |
| Isopentyl isobutyrate<br><br>(Propanoic acid, 2-methyl-, 3-methylbutyl ester) | 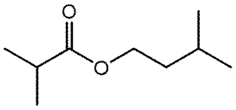 | Isopentyl isobutyrate |
| Allyl acetate<br><br>(Acetic acid, 2-propenyl ester) | 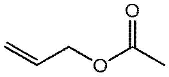 | Allyl acetate |
| Methyl isobutyrate<br><br>(Propanoic acid, 2-methyl-, methyl ester) | 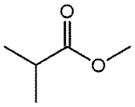 | Methyl isobutyrate |
| Phenylethyl acetate<br><br>(Acetic acid, 1-phenylethyl ester) | 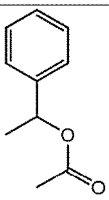 | 1-Phenylethyl acetate |
| Benzaldehyde | 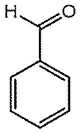 | Benzaldehyde |

*Nomenclature for such compounds generated by ChemBioDraw Ultra, version 13.0

ANTIMICROBIAL COMPOSITIONS AND RELATED METHODS OF USE

This application is a continuation of and claims priority to and the benefit of application Ser. No. 16/416,933 filed May 20, 2019 and issued as U.S. Pat. No. 11,570,986 on Feb. 7, 2023, which was a continuation of and claimed priority to and the benefit of application Ser. No. 15/651,824 filed Jul. 17, 2017 and issued as U.S. Pat. No. 10,292,386 on May 21, 2019, which was a divisional of and claimed priority to and the benefit of application Ser. No. 13/815,839 filed Mar. 15, 2013 and issued as U.S. Pat. No. 9,706,773 on Jul. 18, 2017, which was a continuation in part of and claimed priority to and the benefit of application Ser. No. 12/768,529 filed Apr. 27, 2010 and issued as U.S. Pat. No. 8,728,462, which claimed priority to and the benefit of application Ser. Nos. 61/214,752 filed Apr. 27, 2009; 61/257,319 filed Nov. 2, 2009 and 61/315,611 filed Mar. 19, 2010—each of which is incorporated herein by reference in its entirety.

BACKGROUND OF THE INVENTION

Much progress has been made toward identification and development of biocides for controlling various molds, plant diseases and the like. However, most commercial biocides or pesticides in use are compounds which are classified as carcinogens or are toxic to wildlife and other non-target species. For example, methyl bromide is widely used as a soil fumigant and in the post-harvest treatment of microbial infections. Human toxicity and deleterious environmental effects will ultimately result in discontinued use of methyl bromide and various other synthetic biocides/pesticides. As a result, recent efforts have been directed to the identification and development of natural or biomimetic compositions demonstrating comparable antimicrobial or pesticidal effect.

One such approach relates to endophytes and associated volatile by-products. Endophytes are defined in the art as microorganisms residing in the interstitial spaces of living plant tissue, but are generally not considered to be parasitic. In particular, endophytes found in conjunction with rain forest plants have generated considerable interest for reasons relating to the antibiotic character of their volatile by-products. Several members of the *Muscodor* genus (i.e., *M. albus, M. roseus* and *M. vitigenus*) have been shown to produce volatile by-products exhibiting antibiotic or insecticidal character. However, the respective by-product of each species includes various naphthalene and/or azulene derivatives. Such compounds, together with other by-product components, can be toxic or otherwise unhealthy, and the corresponding mixtures are considered unacceptable for various end use applications. Accordingly, there remains an on-going search in the art to identify natural compositions and to develop biomimetic compositions absent from such compounds, that are safe for human use and demonstrate effective antimicrobial properties.

SUMMARY OF THE INVENTION

In light of the foregoing, it is an object of the present invention to provide flavorings that have antimicrobial compositions and/or methods for their use, thereby overcoming various deficiencies and shortcomings of the prior art, including those outlined above. It will be understood by those skilled in the art that one or more aspects of this invention can meet certain objectives, while one or more other aspects can meet certain other objectives. Each objective may not apply equally, in all its respects, to every aspect of this invention. As such, the following objects can be viewed in the alternative with respect to any one aspect of this invention.

It can be an object of the present invention to provide a *Muscodor* species and a volatile by-product thereof, absent naphthalene and azulene (non-GRAS compounds) related compounds, in conjunction with a methodology for the prevention, inhibition and/or eradication of microbial infection.

It can be another object of the present invention to provide a system comprising such a species or strain thereof and an associated volatile by-product in conjunction with a non-indigenous medium or substrate for use against microbial infection.

It can be another object of the present invention to provide such a system and/or related methodology for use, without limitation, in the context of human and animal food, produce, plants, plant parts, seeds, agricultural crops and other organic materials, packaging, building materials, fibers, cloth, clothing articles, and pharmaceutical and/or medical applications.

It can be another object of the present invention to provide, in the alternative or in conjunction therewith, a range of biomimetic man-made compositions demonstrating antimicrobial activity comparable to such *Muscodor* species.

It can be an object of the present invention to provide one or more such compositions of components edible or otherwise safe for human use and consumption.

It can be another object of the present invention to provide a system, composite or article comprising such a non-natural, biomimetic composition in conjunction with a medium or substrate for the prevention, inhibition and/or eradication of microbial infection. It can be another object of the present invention to provide such a system, composite and/or article for use, in a context of the sort described above or illustrated elsewhere herein.

It can also be an object of the present invention to provide a method for antimicrobial and/or pesticidal treatment comprising such a composition, without limitation as to medium, carrier or substrate.

Other objects, features, benefits and advantages of the present invention will be apparent from this summary and the following descriptions of certain embodiments, and will be readily apparent to those skilled in the art having knowledge of various antimicrobial compositions and related treatments. Such objects, features, benefits and advantages will be apparent from the above as taken into conjunction with the accompanying examples, data, figures and all reasonable inferences to be drawn therefrom, alone or with consideration of the references incorporated herein.

In part, the present invention can be directed to a system comprising at least one of a strain of *M. crispans*, a volatile by-product thereof or vapor of such a volatile by-product and a non-indigenous medium or substrate. Such media or substrates can be as described herein or as would otherwise be understood by those skilled in the art. Regardless, such a strain can be provided in the form of a biologically pure culture, optionally in conjunction with a carrier component suitable for media/substrate contact or end-use application, such a culture sufficiently viable for production of a volatile by-product. In accordance with this invention, a by-product or a modification of a by-product of *M. crispans*, or vapor corresponding thereto, is as compositionally described elsewhere herein.

Accordingly, the present invention can also be directed to using such a system and/or the volatile fungal by-products thereof to provide antimicrobial effect. Such a method can comprise providing a non-indigenous substrate or medium capable of supporting microbial activity or growth; and contacting such a substrate or a medium with a culture of a strain of *M. crispans*, a volatile by-product thereof and/or vapor from such a by-product. In certain embodiments, such contact can comprise such a strain on, about or approximate to such a medium or substrate. In certain other embodiments, a volatile by-product or modifications of a by-product of *M. crispans*, or a corresponding vapor, can infuse or otherwise contact such a medium or substrate.

Without limitation as to any such system or method, such a substrate can be selected from a food or produce item, a packaging component for a food or other perishable item, a fiber, clothing or clothing item, a building or construction component, a plant, plant surface, soil, garbage or refuse. Such contact can be bioactive with respect to microbial presence and/or prophylactic.

In part, the present invention can be directed to a non-naturally occurring antimicrobial composition, whether the components thereof are naturally-derived, chemically-synthesized or a combination thereof. Such a composition can comprise compounds selected from alcohol, aldehyde, ketone, acid and/or acid ester components of a biomimetic *Muscodor* sp. by-product composition, such a composition as can be absent fused aromatic compounds, substituted fused aromatic compounds and hydro derivatives of such compounds. In certain non-limiting embodiments, such a composition can comprise an acid component selected from acetic acid, isobutyric acid, propanoic acid and combinations thereof.

In certain embodiments, the present invention can be directed to a naturally-derived antimicrobial composition comprising a $C_2$-about $C_5$ acid component; a $C_2$—about $C_5$ ester component; and at least two $C_2$-about $C_5$ components isolatable from a volatile by-product of an isolated culture of *Muscodor crispans*, such a composition as can have a pathogen activity profile different from a pathogen activity profile of an isolated, cultured *Muscodor* sp., a volatile by-product thereof and/or a synthetic mixture of such a volatile by-product. Such an acid component can be selected from isobutyric acid, propanoic acid and combinations thereof. Independently, such an ester component can be selected from a $C_4$ ester acetate, a $C_5$ ester acetate and combinations thereof.

In certain other embodiments, such a composition can comprise propanoic acid, and a component selected from a $C_2$-about $C_5$ acid ester, an aldehyde and combinations thereof. In certain such embodiments, an acid ester component can be selected from acetic acid esters, isobutyric acid esters and combinations thereof. One such embodiment can consist essentially of propanoic acid and isobutyl isobutyrate. Another such embodiment can consist essentially of propanoic acid, isoamyl acetate and an aldehyde such as benzaldehyde.

Without limitation, in certain other embodiments, such a composition can comprise about 8-about 10 components otherwise isolatable from a volatile by-product of *M. crispans*. In certain such embodiments, each component of such a composition can be isolatable from such a volatile by-product. As such a composition can be naturally-derived, each such component can be a fermentation product, and fermentation can be selected from bacterial, yeast and/or fungal fermentations. Regardless, each such component of such a composition can be generally recognized as safe for human consumption under Chapter 21 of the United States Code of Federal Regulations and corresponding sections and/or provisions thereof.

Regardless, in certain non-limiting embodiments, such an isolatable component can be isobutyric acid. In certain such embodiments, propanoic acid can be at least in part substituted for isobutyric acid. In such or other non-limiting embodiments, such an isolatable component can be 2-butanone. In certain such embodiments, acetic acid, propanoic acid or a combination thereof can at least in part be substituted for 2-butanone. In such or yet other non-limiting embodiments, such an isolatable component can be ethanol. In certain such embodiments, acetic acid can be at least in part substituted for ethanol. Regardless of the identity or amount of any such acid component, ester component and/or isolatable component, such a naturally-derived composition can comprise a surfactant component. In certain such embodiments, a biosurfactant can be incorporated therewith. Without limitation, a biosurfactant can be a rhamnolipid component selected from a monorhamnolipid, a dirhamnolipid and combinations thereof.

Alternatively, the present invention can be directed to a synthetic, non-naturally derived antimicrobial composition. Such a composition can comprise a $C_2$-about $C_5$ acid component; a $C_2$-about $C_5$ ester component; and at least two $C_2$-about $C_5$ components isolatable from a volatile by-product of an isolated culture of *Muscodor crispans*, such a composition as can have a pathogen activity profile different from a pathogen activity profile of an isolated, cultured *Muscodor* sp. or a volatile by-product thereof. Such acid, ester and/or isolatable components can be as described above or illustrated elsewhere herein. Regardless, such an antimicrobial composition can comprise a surfactant component. In certain such non-limiting embodiments, such a surfactant can be a rhamnolipid component selected from a monorhamnolipid, a dirhamnolipid and combinations thereof.

In part, the present invention can be directed to a biomimetic, antimicrobial composition comprising a liquid mixture of compounds selected from $C_2$ to about $C_5$ alcohols, aldehydes, ketones, acids and acid esters and combinations and sub-combinations thereof, such a composition not isolated from *Muscodor* sp. As discussed elsewhere herein, such a liquid mixture can be volatile at room and/or ambient temperatures. With respect to such a composition and the compounds thereof, the term "about" can mean, as would be understood by those skilled in the art, carbon and/or methylene homologs with corresponding molecular weight and/or structural isomerism limited only by mixture with one or more other components, compounds and at least partial room/ambient temperature volatility of the resulting composition. With respect to certain non-limiting embodiments, such a composition can comprise alcohol, aldehyde, ketone, acid and acid ester compounds selected from components of a biomimetic *M. crispans* by-product composition, of the sort described below. Such a composition can comprise compounds chemically synthesized, compounds isolated from bacterial fermentation and combinations of such compounds. In certain such embodiments, such a composition can comprise an acid component selected from acetic acid, isobutyric acid, propanoic acid and combinations thereof.

In part, the present invention can also be directed to a non-naturally-occurring, whether naturally-derived and/or chemically-synthesized, antimicrobial composition comprising compounds selected from $C_2$ to about $C_5$ alcohols, aldehydes, ketones, acids and acid esters and combinations and sub-combinations of such compounds, such selected compounds generally recognized as safe ("GRAS") for human consumption, such designation as provided in Chapter 21 of the United States Code of Federal Regulations and corresponding sections and/or provisions thereof. In certain non-limiting embodiments, such compounds can be selected from alcohol, ketone, acid and/or acid ester components of a biomimetic *M. crispans* by-product composition. In certain embodiments, a microbe activity/mortality profile thereof differs from that of either *M. crispans* or *M. albus*, a volatile by-product thereof and/or corresponding synthetic by-product compositions thereof. Regardless, in certain such embodiments, such a composition can comprise an acid component selected from acetic acid, isobutyric acid, propanoic acid and combinations thereof.

In part, the present invention can comprise a composition comprising a composition of this invention; and a surfactant component, such a surfactant component alone or as can be incorporated into a carrier component. In certain embodiments, such a surfactant can be a biosurfactant, such a biosurfactant as can be a rhamnolipid component selected from a monorhamnolipid, a dirhamnolipid and combinations thereof.

In part, the present invention can also be directed to a system or composite comprising an inventive composition and a substrate or medium component. Such a composition can be as described above or illustrated elsewhere herein. Without limitation, a substrate can be selected from a food or produce item, a packaging component (e.g., a film or wrapper) for a food or other perishable item, a fiber, cloth or clothing item, a building or construction component, a human tissue, a plant, plant surface, soil, and garbage or refuse. In certain embodiments, such a composition, whether liquid or gaseous, can be incorporated or otherwise in contact with such a medium, substrate or substrate surface.

In part, the present invention can be directed to an article of manufacture, such an article as can comprise a solid carrier component and a volatile antimicrobial composition absorbed in, adsorbed on, coupled to or otherwise incorporated therewith. Such an antimicrobial composition can comprise propanoic acid; and a component selected from a $C_2$-about $C_5$ acid ester, an aldehyde and combinations thereof. In certain embodiments, such an acid ester can be selected from acetic acid esters, isobutyric acid esters and combinations thereof; and/or an aldehyde component can be selected from a $C_2$-about $C_8$ aldehyde component. In certain such embodiments, an acid ester can be isobutyl isobutyrate; or such an aldehyde component can be benzaldehyde. Regardless, such an antimicrobial composition can be incorporated with a carrier component comprising a clay. In certain such embodiments, such a carrier component can comprise a bentonite clay. Regardless, such a composition can comprise one or more optional components or adjuvants, including but not limited to a rhamnolipid component.

Alternatively, such an article of manufacture can be considered with an incorporated antimicrobial composition as can comprise propanoic acid and a $C_2$-about $C_5$ acid ester comprising at least one of an alkylcarbonyl group, RC(O)—, wherein R comprises an isopropyl, $(CH_3)_2CH$—, moiety, and an alkoxy group, —OR', wherein R' comprises an isopropyl, —$CH(CH_3)_2$, moiety. In certain embodiments, such an acid ester can be selected from isoamyl acetate, isobutyl isobutyrate and a combination thereof. In certain such embodiments, such an antimicrobial composition can consist of propanoic acid and isobutyl isobutyrate. In certain other such embodiments, such a composition can consist of propanoic acid, isoamyl acetate and benzaldehyde. Regardless, such a solid carrier component can comprise a clay.

Accordingly, such an article can comprise a solid carrier component comprising a bentonite clay, and an antimicrobial composition incorporated therewith. Without limitation, such an antimicrobial composition can be selected from a composition consisting essentially of propanoic acid and isobutyl isobutyrate; and a composition consisting essentially of propanoic acid, isoamyl acetate and benzaldehyde.

In part, the present invention can also be directed to an article of manufacture comprising granules of a solid carrier component and an antimicrobial composition incorporated therewith. Such a composition can comprise a $C_2$-about $C_5$ acid component; at least one $C_2$-about $C_5$ component isolatable from a volatile by-product of an isolated culture of *Muscodor crispans* grown on potato dextrose agar; and a component selected from at least one $C_2$-about $C_5$ acid ester, an aldehyde and combinations thereof. As relates to such an article, such composition-incorporated solid carrier component granules can be provided in a vapor-permeable enclosure.

In certain embodiments, such solid carrier and antimicrobial compositions can be as discussed above or illustrated elsewhere herein. In certain such embodiments, such an antimicrobial composition can be about 0.01 wt. % to about 10.0 wt. % of such an article. In certain such embodiments, such a composition can be about 0.20 wt. % to about 10.0 wt. %. In yet other embodiments, such a composition can be about 1.0 wt. % to about 3 wt. % of such an article. Without limitation as to solid carrier component or antimicrobial composition incorporated therewith, such an enclosure can comprise a woven mesh and/or non-woven material as can be configured as a flexible bag or pouch. Regardless, such an article of manufacture can be provided in a container with a perishable food item.

Accordingly, this invention can also be directed toward a method of microbial or insect treatment, prevention, inhibition, eradication and/or to otherwise affect microbial or insect activity. Such a method can comprise providing a composition of this invention, including but not limited to one or more compositions of the sort illustrated herein; and contacting a microbe or insect or an article/substrate capable of supporting microbial or insect activity with such a composition in an amount at least partially sufficient to affect microbial or insect activity. Such a microbe (e.g., a fungus, bacterium or virus) or insect can be in a medium, on or about a surface of a substrate of the sort discussed above. Accordingly, such contact can be direct and/or upon volatilization of such a composition. Regardless, such treatment can be active with respect to microbial or insect presence and/or prophylactic. As illustrated elsewhere herein, treatment can be considered in the context of microbial or insect death and/or inhibited growth or activity.

In part, the present invention can also be directed to a method of affecting microbial activity. With respect to such a method, the present invention can comprise providing an article of the sort described above or illustrated elsewhere herein; and contacting the vapor of an antimicrobial composition of such an article with a microbe and/or a food item capable of supporting microbial activity, such a composition as can be in an amount sufficient to affect microbial activity. In certain embodiments, such a food item can comprise post-harvest produce. Together with an article of this invention, such produce as can be optionally introduced to a container at a point along a produce supply chain. Without limitation, produce introduction can be at a point of harvest, a point of processing, a point of wholesale distribution, a point of retail sale, and combinations thereof. Regardless of produce or point of introduction, such an antimicrobial composition can be as described above or illustrated elsewhere herein.

In accordance with certain embodiments of this invention, compositions comprising certain food and flavor compounds (FFCs) are especially inhibitory and/or lethal to certain pathogenic fungi, bacteria and other microbes of agricultural, medicinal, or commercial or industrial concern. Such compositions can be distinguished over any previous mixture containing biologically derived compounds: for instance, the present compositions do not contain any naphthalene or azulene (non-GRAS compounds) derived substances. Conversely, such compositions can comprise a mixture of organic compounds, each of which otherwise considered (i.e., GRAS) a food or flavoring substance.

The present invention demonstrates the nature of such compositions, their preparation and application to various items (e.g., without limitation, food, fibers, implements and construction surfaces) to preserve their integrity and prevent destruction by various fungi (molds and other microorganisms). Such compositions can also be applied to building structures, plant parts and even clothing items for their preservation. Further, as demonstrated below, such a composition can negatively affect *Mycobacterium tuberculosis*—the microorganism that causes tuberculosis—including at least 3 strains that are otherwise drug resistant.

BRIEF DESCRIPTION OF THE DRAWINGS

FIG. 9 provides two embodiments of a rhamnolipid component, designated R1 and R2 for the respective mono- and dirhamnolipid structures, which can be used alone or in combination of one with the other, as described in several of the followings examples, in accordance with certain non-limiting embodiments of this invention.

FIG. 10 provides alternate nomenclature and structures of FFCs useful in conjunction with various antimicrobial compositions, in accordance with certain non-limiting embodiments of this invention.

DETAILED DESCRIPTION OF CERTAIN EMBODIMENTS

Figure 1:
FIG. 1. Photographs illustrating the killing effect of the FFCs against clinical cultures of drug resistant *Mycobacterium tuberculosis* after exposure for 2 days.

As illustrated by several non-limiting embodiments, this invention relates to the use of a new species of *Muscodor* and/or its volatile by-products and the development of non-natural, laboratory-prepared, biomimetic compositions comprising common food and flavor compounds that, when incorporated into various media, applied to surfaces, or introduced to an atmosphere, space or volume, bring about a decontamination of the desired surface medium or volume of otherwise unsightly, harmful, and/or pathogenic microorganisms including plant fungi and the causal agent of tuberculosis. The invention has extremely important implications and applications to modern agriculture, human medicine, food sciences, and industry. The compositions of this invention are not obvious as having antimicrobial properties given the fact that no one individual ingredient, in and of itself, is biologically active. A synergistic combination of component ingredients manifests the full potential antimicrobial activity.

With respect to the use of such a *Muscodor* species, a volatile by-product thereof or a non-naturally-occurring biomimetic composition comprising FFCs, contact can be direct or by exposure to a vapor associated with such a species, by-product of biomimetic composition. As illustrated below, in the context of certain embodiments, while vapor exposure can inhibit growth, direct microbial contact may be required for bacterial or fungal death.

Regardless of mode of contact, the compositions of this invention can be laboratory-made, comprising chemically-synthesized components, naturally-derived components or a combination of such synthetic and natural components. Regardless, such compositions can be biomimetic with respect to the effect of a *Muscodor* by-product on a particular bacterial or fungal species. Alternatively, such a composition, by relative concentration or selection of any one or more FFC component thereof, can demonstrate varied or enhanced antimicrobial activity, as compared to a *Muscodor* fungal by-product.

In certain such embodiments, such a composition can be on, or as can be applied to, a substrate or medium comprising a proteinaceous or cellulosic component which can, is capable of or does support microbe growth. Without limitation, certain embodiments can comprise plants, plant components (e.g., roots, stems, leaves or foliage, produce and the like) and any originating shoots or seeds. In particular, without limitation, such compositions can be on any plant produce, whether termed a fruit, vegetable, tuber, flower, seed or nut, whether before or post-harvest. Certain such plants and/or produce therefrom are recognized in the art, alone or collectively, as agricultural crops. Accordingly, in certain embodiments, a composition of this invention can be on or applied to such a crop at any time during development, pre-harvest and/or post-harvest. Likewise, a composition of this invention can be applied to or incorporated into a beverage, food (e.g., human, pet and/or animal) product or article of manufacture which can, is capable of or does support microbe growth.

In certain other embodiments of this invention, such a composition can be on, or as can be applied to, a substrate or surface supporting or supportive of microbe (e.g., yeast and/or fungi bacteria and/or virus) growth. Accordingly, such a substrate or surface can comprise any material which can, is capable of or does support microbe growth. Such substrates include but are not limited to wood, ceramics, porcelain, stone, plaster, drywall, cement, fabrics, leather, plastics and the like.

In certain other embodiments, various compositions of this invention can be on, in contact with, or as applied or administered to a substrate or surface comprising mammalian or human tissue, including but not limited to nails, hair, teeth or mouth, skin and other cellular material, in the context of a pharmaceutical or personal care or hygiene formulation for the treatment or prevention of microbial growth or infection. Representative compositions are described, below, in terms at least in part applicable to one or more other embodiments.

An endophytic fungus was recovered from inside the tissues of a wild pineapple plant (*Ananas ananassoides*) growing in the Bolivian Amazon. Ultimately, it was shown to produce a mixture of volatile compounds having antimicrobial activities. Using molecular techniques, the fungus was found to possess sequence similarities to members of the *Muscodor* genus. These fungi are known to produce volatile organic compounds that can act as anti-microbials which are effective against both human and plant pathogens. Members of the *Muscodor* species have been identified utilizing methods such as Phylogenetic Character mapping employing 18S rDNA plus ITS-5.8S rDNA sequence analyses. The sequences found in the present fungus and other *Muscodor* spp. were BLAST searched in GenBank, and compared to other fungi (Bruns et al., 1991; Reynolds and Taylor 1993; Mitchell et al., 1995; Guano et al., 1999; Taylor et al., 1999). Ultimately it was determined that these isolates are related to *Xylaria* (Worapong et al., 2001a&b). All isolated taxa that belong to *Muscodor* have similar characteristics, such as growing relatively slowly, possessing a felt-like mycelium, producing biologically active volatile compounds, and causing no harm to the plants in which they originally resided. Finally, they each share closely similar rDNA sequences (Ezra et al., 2004).

Although the present fungus shared all of the same common features mentioned above, there were a number of different aspects to the taxon which distinguished it from all other *Muscodor* spp. and isolates. As illustrated more fully in the following examples, these unique characteristics support establishment of the present fungus as a new species. The name proposed for this novel endophytic fungus is *Muscodor crispans*.

As analyzed by GC/MS, the isolated fungus produced alcohols, esters and small molecular weight acids, in the gas phase, when grown on potato dextrose agar (PDA). As shown in Table 1, below, such compounds include propanoic acid, 2-methyl; 1-butanol, 3-methyl, acetate; 1-butanol, and ethanol. Neither naphthalene nor azulene derivatives (non-GRAS compounds) were produced by this organism when grown on PDA, distinguishing it from all other *Muscodor* spp. studied thus far. The odor produced by the fungus becomes noticeable after about 1 week and seems to increase with time up to and including at least three weeks. As illustrated below, the volatiles of this fungus possess inhibitory and lethal bioactivity against a number of plant and human pathogens using the standard bioassay technique (Strobel et al., 2001).

TABLE 1

| Retention Time Min. | Compound | MW |
|---|---|---|
| 2:05 | Acetaldehyde | 44.03 |
| 3:40 | Ethyl Acetate | 88.05 |
| 3:51 | 2-Butanone | 72.06 |
| 4:08 | Propanoic acid, 2-methyl-, methyl ester | 102.07 |
| 4:18 | Ethanol | 46.04 |
| 5:29 | Acetic acid, 2-methylpropyl ester | 116.08 |
| 6:39 | Propanoic acid, 2-methyl-, 2-methylpropyl ester | 144.12 |
| 6:46 | 1-Propanol, 2-methyl- | 74.07 |
| 6:52 | 2-Butenal, 2-methyl-, (E)- | 84.06 |
| 7:12 | 1-Butanol, 3-methyl-, acetate | 130.10 |
| 8:18 | Hexane, 2,3-dimethyl- | 114.14 |
| 8:21 | Propanoic acid, 2-methyl-, 2-methylbutyl ester | 158.13 |
| 8:31 | 1-Butanol, 3-methyl- | 88.09 |
| 13:37 | Propanoic acid, 2-methyl- | 88.05 |
| 14:41 | Formamide, N-(1-methylpropyl)- | 101.08 |
| 16:44 | Acetic acid, 2-phenylethyl ester | 164.08 |
| 20:44 | Cyclohexane, 1,2-dimethyl-3,5-bis(1-methylethenyl)- | 192.19 |

As discussed above, the present invention includes use of *M. crispans* and/or a volatile by-product thereof in conjunction with a non-indigenous medium, substrate and/or volume for antimicrobial effect. Such use and/or applications can be as described herein or as would otherwise be understood by those skilled in the art, including but not limited to use and application of the sort described in U.S. Pat. No. 6,911,338, the entirety of which is incorporated by reference.

Alternatively, a wide range of natural and synthetic biomimetic compositions can be used with comparable or enhanced effect or, as evidenced by one or more embodiments, to provide results heretofor not available through use of either the fungus or its volatile by-product. As a departure from the prior art and the by-product of *M. crispans*, such antimicrobial compositions can comprise food and flavor compounds generally recognized as safe for human use and consumption. Representative thereof, several non-limiting biomimetic compositions are provided in Tables 2-7, below. Various other compositions can comprise combinations of compounds selected from any one or more of Tables 2-7. (See, e.g., examples 52-56.) Alternatively, any such composition can comprise a component compound in addition to or as replacement for any compound listed, to enhance volatility or modify any other end-use or performance property. In certain such compositions, such a replacement or additional compound can have a GRAS designation and/or be so designated at levels utilized—such compositions as can be considered essentially free of any component or material that would not be generally recognized as safe (GRAS) under the applicable United States Code of Federal Regulations. Such compositions can, alternatively, include a component found in a volatile by-product of *M. crispans* and/or not in a volatile by-product of another *Muscodor* sp.

Each such compound can be provided within an effective concentration or percentage range and is either commercially available or can be prepared by those skilled in the art. With regard to the latter, fermentation techniques can be used to naturally prepare and isolate such compounds. Alternatively, such compounds can be chemically synthesized. With respect to several non-limiting embodiments of this invention, each compound of Tables 2-7 can be obtained as a fermentation product, such products and corresponding compositions as are available under the Flavorzon trademark from Jeneil Biotech, Inc. of Saukville, Wisconsin.

TABLE 2

| A biomimetic composition of this invention comprising: Compound |
|---|
| Acetaldehyde |
| Ethyl Acetate |
| 2-Butanone |
| Propanoic acid, 2-methyl-, methyl ester |
| Ethanol |
| Acetic acid, 2-methylpropyl ester |
| Propanoic acid, 2-methyl-, 2-methylpropyl ester |
| 1-Propanol, 2-methyl- |
| 1-Butanol, 3-methyl-, acetate |
| Propanoic acid, 2-methyl-, 2-methylbutyl ester |
| 1-Butanol, 3-methyl- |
| Propanoic acid |
| Acetic acid, 2-phenylethyl ester |

TABLE 3

| A biomimetic composition of this invention comprising: Compound |
|---|
| Acetaldehyde |
| Ethyl Acetate |
| 2-Butanone |
| Propanoic acid, 2-methyl-, methyl ester |
| Ethanol |
| Acetic acid, 2-methylpropyl ester |
| Propanoic acid, 2-methyl-, 2-methylpropyl ester |
| 1-Propanol, 2-methyl- |
| 1-Butanol, 3-methyl-, acetate |
| Propanoic acid, 2-methyl-, 2-methylbutyl ester |
| 1-Butanol, 3-methyl- |
| Propanoic acid, 2-methyl- |
| Acetic acid, 2-phenylethyl ester |
| Propanoic Acid |

TABLE 4

| A biomimetic composition of this invention comprising: Compound |
|---|
| Acetaldehyde |
| Ethyl Acetate |
| 2-Butanone |
| Propanoic acid, 2-methyl-, methyl ester |
| Acetic Acid |
| Acetic acid, 2-methylpropyl ester |
| Propanoic acid, 2-methyl-, 2-methylpropyl ester |
| 1-Propanol, 2-methyl- |
| 1-Butanol, 3-methyl-, acetate |
| Propanoic acid, 2-methyl-, 2-methylbutyl ester |
| 1-Butanol, 3-methyl- |
| Propanoic acid, 2-methyl- |
| Acetic acid, 2-phenylethyl ester |

TABLE 5

| A biomimetic composition of this invention comprising: Compound |
|---|
| Acetaldehyde |
| Ethyl Acetate |
| Acetic Acid |
| Propanoic acid, 2-methyl-, methyl ester |
| Ethanol |
| Acetic acid, 2-methylpropyl ester |
| Propanoic acid, 2-methyl-, 2-methylpropyl ester |
| 1-Propanol, 2-methyl- |
| 1-Butanol, 3-methyl-, acetate |
| Propanoic acid, 2-methyl-, 2-methylbutyl ester |
| 1-Butanol, 3-methyl- |
| Propanoic acid, 2-methyl- |
| Acetic acid, 2-phenylethyl ester |

TABLE 6

| A biomimetic composition of this invention comprising: Compound |
|---|
| Acetaldehyde |
| Ethyl Acetate |
| Propanoic Acid |
| Propanoic acid, 2-methyl-, methyl ester |
| Ethanol |
| Acetic acid, 2-methylpropyl ester |
| Propanoic acid, 2-methyl-, 2-methylpropyl ester |
| 1-Propanol, 2-methyl- |
| 1-Butanol, 3-methyl-, acetate |
| Propanoic acid, 2-methyl-, 2-methylbutyl ester |
| 1-Butanol, 3-methyl- |
| Propanoic acid, 2-methyl- |
| Acetic acid, 2-phenylethyl ester |

TABLE 7

A biomimetic composition of this invention comprising various combinations of compounds selected from or comprising the following compounds:

| % | Compound |
|---|---|
| about 0.1-about 10 | Acetaldehyde |
| about 0.5-about 25 | Ethyl Acetate |
| about 0.1-about 15 | 2-Butanone |
| about 4-about 99 | Propanoic acid, 2-methyl-, methyl ester |
| about 1.5-about 40 | Ethanol |
| about 0.1-about 10 | Acetic acid, 2-methylpropyl ester |
| about 0.1-about 15 | Propanoic acid, 2-methyl-, 2-methylpropyl ester |
| about 0.1-about 10 | 1-Propanol, 2-methyl- |
| about 0.5-about 25 | 1-Butanol, 3-methyl-, acetate |
| about 0.5-about 25 | Propanoic acid, 2-methyl-, 2-methylbutyl ester |
| about 2-about 50 | 1-Butanol, 3-methyl- |
| about 10 to about 99 | Propanoic acid, 2-methyl- |
| about 0.1-about 10 | Acetic acid, 2-phenylethyl ester |

With respect to any FFC composition of this invention, it is contemplated that any compound component thereof—including any compound component described referenced or inferred herein, such as but not limited to any component in Tables 1-7 and 10 and structural isomers and/or carbon and methylene homologs thereof—can be present in an amount or a range separate and apart from any other compositional component. Accordingly, without limitation, each such compound component can be present in an amount of or a range of about 0.1 wt. %, (or less) about 0.2 wt. %, about 0.3 wt. %, or about 0.4 wt. %, . . . or/to about 1.0 wt. %, about 1.1 wt. %, about 1.2 wt. %, about 1.3 wt. %, or about 1.4 wt. % . . . or/to about 2.0 wt. %, about 2.1 wt. %, about 2.2 wt. %, about 2.3 wt. %, or about 2.4 wt. % . . . or/to about 3.0 wt. %, about 3.1 wt. %, about 3.2 wt. %, about 3.3 wt. %, or about 3.4 wt. % . . . or/to about 4.0 wt. %, about 4.1 wt. %, about 4.2 wt. %, about 4.3 wt. %, or about 4.4 wt. % . . . or/to 5.0 wt. %, about 5.1 wt. %, about 5.2 wt. %, about 5.3 wt. %, or about 5.4 wt. % . . . or/to about 6.0 wt. %, about 6.1 wt. %, about 6.2 wt. %, about 6.3 wt. %, or about 6.4 wt. % . . . or/to about 7.0 wt. %, about 7.1 wt. %, about 7.2 wt. %, about 7.3 wt. %, or about 7.4 wt. % . . . or/to about 8.0 wt. %, about 8.1 wt. %, about 8.2 wt. %, about 8.3 wt. %, or about 8.4 wt. % . . . or/to about 9.0 wt. %, about 9.1 wt. %, about 9.2 wt. %, about 9.3 wt. %, or about 9.4 wt. % . . . or/to about 10.0 wt. %; and or/to about 10.1 wt. % . . . or/to about 20.0 wt. %, in accordance with such incremental variation; or/to about 20.1 wt. % . . . or/to about 30.0 wt. %, in accordance with such incremental variation; or/to about 30.1 wt. % . . . or/to about 40.0 wt. %, in accordance with such incremental variation; or/to about 40.1 wt. % . . . or/to about 50.0 wt. %, in accordance with such incremental variation; or/to about 50.1 wt. % . . . or/to about 60.0 wt. %, in accordance with such incremental variation; or/to about 60.1 wt. % . . . or/to about 70.0 wt. %, in accordance with such incremental variation; or/to about 70.1 wt. % . . . or/to about 80.0 wt. %, in accordance with such incremental variation; or/to about 80.1 wt. % . . . or/to about 90.0 wt. %, in accordance with such incremental variation; or/to about 90.1 wt. % . . . or/to about 99.9 wt. % (or more), in accordance with such incremental variation. Likewise, without limitation, any composition of this invention—regardless of identity or amount of any particular compound component or combination—can be present in amount (wt. %) or a wt. % range incrementally variable, as described above, from 0.1 wt. % to 99.9 wt. % of any composition or medium (e.g., within any range from about 0.1 wt. % to about 1.0 wt. %, about 2.0 wt. %, about 4.0 wt. % or to about 10.0 wt. %) therein incorporated or article or substrate thereon applied.

Unless otherwise indicated, all numbers expressing amounts, concentrations or quantities of components or ingredients, properties such as molecular weight, reaction conditions, and so forth used in the specification and claims are to be understood as being modified in all instances by the term "about." Accordingly, unless indicated to the contrary, the numerical parameters set forth in this specification and attached claims are approximations that may vary depending upon the desired properties sought to be obtained by the present invention. At the very least, and not as an attempt to limit application of the doctrine of equivalents to the scope of claims, each numerical parameter should at least be construed in light of the number of reported significant digits and by applying ordinary rounding techniques.

Notwithstanding that the numerical ranges and the parameters setting forth the broad scope of this invention are approximations, the numerical values set forth and the examples are reported as precisely as possible. Any numerical value, however, may inherently contain a certain error resulting from the standard deviation found in a respective testing measurement.

The compositions and methods of this invention can suitably comprise, consist of or consist essentially of any compound component or amount/concentration thereof disclosed, referenced or inferred herein—including but not limited to any compound component in Tables 1-7 and 10, together with any structural isomers thereof, carbon and/or methylene homologs of any such alcohol component, aldehyde component, ketone component, acid component and/or ester component, whether the acid-derived and/or alcohol-derived moiety thereof. Regardless of amount/concentration, each such compound component or moiety/substituent thereof is compositionally distinguishable, characteristically contrasted and can be used in conjunction with the present compositions and methods separate and apart from another such component amount/concentration or another compound component (or moiety/substituent) or amount/concentration. Accordingly, it should be understood that the inventive compositions and/or methods, as illustratively disclosed herein, can be practiced or utilized with change in amount or concentration in the absence of any one component compound (or moiety and/or substituent thereof), such compound (or moiety/substituent thereof) or amount/concentration thereof which may or may not be specifically disclosed, referenced or inferred herein, the change or absence of which may or may not be specifically disclosed, referenced or inferred herein.

In preferred embodiments, a biologically effective composition of such FFCs (prepared as a liquid mixture) is readily volatilized at room temperature and diffuses throughout an enclosed space to effectively inhibit and/or kill unwanted contaminating fungi (molds) on surfaces that are desired to be free of such harmful microbes. The mixture maybe applied as a spray (e.g., can with ingredients under pressure) or simply placed in a container and allowed to evaporate in the closed container or sealed bag.

Regardless, the FFC compositions of this invention can be incorporated into a variety of end-use compositions, limited only by application. Such compositions include but are not limited to those directed to human/animal food or nutrient, personal hygiene, healthcare, agricultural, industrial, residential, medical and consumer applications. In certain non-limiting embodiments, an FFC composition and/or component(s) thereof can be present at about 0.1 wt. % or less to about 99.9 wt. % or more of a particular end-use composition. Such level of incorporation is limited only by desired antimicrobial effect and/or formulation considerations.

The present FFC compositions, under effective dose levels, are effective in killing many plant pathogens, fungi that can cause food spoilage, microbes that can cause major human diseases and microbes that can foul work surfaces, homes and other buildings. A non-exclusive list of such applications is below:

1. For treatment of cheeses in storage or in preparation to control unsightly mold contamination of surfaces and eventual spoilage of the cheese blocks.

2. For treatment of various plant parts in storage including roots, tubers, stems, seeds and other organs that may be eventually used for food preparation of for planting and re-vegetation or agricultural purposes.

3. For use in decontaminating buildings that may either have moldy surfaces or be infested to a point that a mold problem may develop.

4. For use in the preservation of garbage whilst it is in shipment over long sea hauls from one port to another for eventual fermentation into energy related products.

5. For the decontamination of soils that may harbor microbes that are potential plant pathogens.

6. For the treatment of patients with tuberculosis and other mycobacterium infections.

7. For treatment to control nasal infections and to clear nasal passage ways.

8. For combining with specifically designed polymers that can be used to wrap and thus preserve materials including foods, fibers and other items for longer term safe storage.

More generally, the compositions of this invention can be used to inhibit the growth of or kill an organism selected from the group consisting of a fungus, a bacterium, a microorganism and a range of other microbes or pests. Using methods well known to those of skill in the art, such a composition is contacted with the organism in an amount at least partially effective to kill or inhibit the growth of the organism. Alternatively, it can be used to treat human or animal waste, e.g., as a component of a waste water or solid management or treatment. Such compositions also are useful to decontaminate human and animal waste, e.g., decrease or remove bacterial and fungal contamination. Yet further, such a composition can be used to treat or prevent mold on building materials and in buildings by contacting the building, the building materials, or the spaces between the building materials with an effective amount thereof or vapors therefrom. For the purpose of illustration only, an effective amount of such a composition can be used alone or in combination with other fumigants or active agents in a room or alternatively, during whole building fumigations.

When used in agricultural applications, the invention provides a method for treating or protecting fruit, seeds, plants or the soil surrounding the plants from an infestation by an organism such as a fungus or a bacterium, by contacting the microorganism with an effective amount of one or more compositions of the sort described herein.

As discussed above, the present invention provides a method of preventing, treating, inhibiting and killing a bacterial, fungal, viral and/or other microbial infection. Such a method can comprise administering to an article, animal/mammal or plant substrate, having such an infection or growth or capable of supporting such an infection or growth, an effective amount of an inventive composition—alone or as can be incorporated into a composition or formulation. Accordingly, the present invention provides one or more compositions for pharmaceutical, personal (e.g., without limitation, cosmetic), industrial and/or agricultural use.

Microbial treatment can be achieved by contacting a bacterium, fungus, virus and/or other microbe with an effective amount of an inventive composition. Contacting may take place in vitro or in vivo. “Contacting” means that such a composition of this invention and such a microbe are brought together in a manner sufficient to prevent, inhibit and/or eliminate microbial infection and/or growth. Amounts of such a composition effective for such treatment may be determined empirically, and making such determinations is within the skill in the art. Inhibition includes both reduction and elimination of microbial growth/activity.

Compositions of this invention may be administered to or contacted with a human, animal or plant, or article substrate surface by any suitable route, including but not limited to orally or nasally (e.g., for pharmaceutical or personal care applications), and topically, as by powders, granules, liquids, sprays, ointments, lotions or creams. Accordingly, compositions of the invention can comprise the respective component compounds in admixture with one or more acceptable carriers and, optionally, with one or more other compounds or other materials. Such a carrier should be “acceptable” in the sense of being compatible with the other components/ingredients of the formulation and not deleterious to the desired effect or application.

Regardless of the route of delivery, treatment or administration selected, the inventive compositions can be formulated to provide acceptable concentrations or dosage forms by conventional methods known to those of skill in the art. The amount or concentration of any such composition or component thereof, with or without a carrier, will vary depending upon the target microbe/substrate/article being treated, the particular mode of administration/delivery and all of the other factors described above. The amount combined with a carrier material will generally be that amount of such a composition providing the lowest or a minimal concentration effective to produce a desired antimicrobial effect.

The relative amounts or concentrations of an FFC composition and another optional component in the compositions of the present invention can vary widely within effective ranges, as demonstrated in the examples that follow. The concentrations and/or doses utilized are preferably selected to achieve an enhanced or increased activity over individual prior art components alone and/or to maximize the activity of the composition at the lowest effective component concentration(s). Accordingly, the weight ratios and/or percent concentrations yielding such enhanced activity depend not only on the specific FCC composition utilized, but on the specific end-use application of the composition including, but not limited to, climate, soil composition, nature of the substrate, article and/or microbial host to be treated and/or potential exposure to a particular microbe.

Methods of preparing formulations or compositions include the step of bringing a composition of this invention, or one or more component compounds, into association with a carrier and, optionally, one or more accessory ingredients. In general, the formulations are prepared by bringing such a composition/component into association with a carrier (e.g., a liquid or finely divided solid carriers) and, if desired, shaping the product.

Formulations relating to the invention, whether a composition of this invention or any article of manufacture incorporating such a composition, may be in the form of capsules, cachets, pills, tablets, powders, granules, paste or as a solution or a suspension in an aqueous or nonaqueous liquid, or as an oil-in-water or water-in-oil liquid emulsion, or as an elixir or syrup, or as pastilles (using an inert base, such as gelatin and glycerin, or sucrose and acacia) and/or as washes (e.g., mists, spray or mouth) and the like, each containing a predetermined amount of an inventive composition or components thereof.

In other solid such formulations (e.g., capsules, tablets, pills, dragees, powders, granules and the like), a composition of this invention can be mixed with one or more other active ingredients and/or acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethyl-cellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such as talc, calcium stearate, magnesium stearate, solid polyethylene glycols, sodium lauryl sulfate, and mixtures thereof; and (10) coloring agents. In the case of capsules, tablets and pills, the compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered active ingredient(s) moistened with an inert liquid diluent.

The tablets, and other solid forms of such compositions or articles incorporating such compositions, such as dragees, capsules, pills and granules, may optionally be scored or prepared with coatings and shells, such as enteric coatings and other coatings well known in the formulating art. They may also be formulated so as to provide slow or controlled release of the active ingredient(s) therein using, for example, hydroxypropylmethyl cellulose in varying proportions to provide the desired release profile, other polymer matrices, liposomes and/or microspheres. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient(s) can also be in microencapsulated form.

Liquid forms for use or administration of this invention include pharmaceutically- or otherwise-acceptable emulsions, mixtures, microemulsions, solutions (including those in distilled or purified water), suspensions, mists, syrups and elixirs. In addition to an inventive composition or compound component(s) thereof, a liquid form may contain inert or other diluents commonly used in the art, such as, for example, water or other solvents, solubilizing agents and emulsifiers, such as ethyl alcohol, isopropyl alcohol, ethyl carbonate, ethyl acetate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, such compositions and/or related articles can also include adjuvants such as but not limited to wetting agents, emulsifying and suspending agents (e.g., sticker and spreader agents for agricultural application), coloring, perfuming and one or more other preservative agents. Suspensions can comprise suspending agents as, for example, ethoxylated isostearyl alcohols, polyoxyethylene sorbitol and sorbitan esters, microcrystalline cellulose, aluminum metahydroxide, bentonite, agar and tragacanth, and mixtures thereof.

Formulations of compositions of this invention and/or articles or products incorporating such inventive compositions for substrate or topical (e.g., in the context of a personal care or hygiene product) administration/delivery of this invention, include powders, sprays, ointments, pastes, creams, lotions, gels, solutions, patches and inhalants. Such ointments, pastes, creams and gels may contain, in addition to an inventive composition of this invention, excipients, such as animal and vegetable fats, oils, waxes, paraffins, starch, tragacanth and other gums, cellulose derivatives, polyethylene glycols, silicones, bentonites, silicic acid, talc and zinc oxide, or mixtures thereof. Likewise, powders and sprays can contain excipients such as lactose, talc, silicic acid, aluminum hydroxide, calcium silicates and polyamide powder, or mixtures of these substances. Sprays can additionally contain customary propellants such as volatile unsubstituted hydrocarbons, such as butane and propane, or be delivered under positive air pressure.

Examples of suitable aqueous and nonaqueous carriers which may be employed in the compositions of the invention include water, ethanol, polyols (such as glycerol, propylene glycol, polyethylene glycol, and the like), and suitable mixtures thereof, vegetable oils, such as olive oil, and organic esters, such as ethyl oleate. Proper fluidity can be maintained, for example, by the use of coating materials, such as lecithin, by the maintenance of the required particle size in the case of dispersions, and by the use of surfactants.

Depot forms of articles or products incorporating a composition of this invention can be made by forming microencapsule matrices of an active ingredient(s) in biodegradable polymers such as polylactide-polyglycolide. Depending on the ratio of the active ingredient(s) to polymer, and the nature of the particular polymer employed, the rate of release of the active ingredient(s) can be controlled. Examples of other biodegradable polymers include poly(orthoesters) and poly(anhydrides). Depot injectable formulations are also prepared by entrapping the active ingredient(s) in liposomes or microemulsions which are compatible with body tissue.

Further, the compositions of the present invention and/or articles or products incorporating such a composition can comprise additional chemical and/or biological, multi-site and/or single site antimycotic or antifungal, antibacterial and antimicrobial agents, of a similar and/or different modes of action, as will be well known to those skilled in the art. Such agents can include, but are not limited to, potassium bicarbonate, silica, copper or sulfur-based compounds and/or botanical oils (e.g., neem oil). Further, such agents can include, but are not limited to azoles; polyenes, such as amphotericin B and nystatin; purine or pyrimidine nucleotide inhibitors, such as flucytosine; polyoxins, such as nikkomycins; other chitin inhibitors, elongation factor inhibitors, such as sordarin and analogs thereof; inhibitors of mitochondrial respiration, inhibitors of sterol biosynthesis and/or any other fungicidal or biocidal composition known to those skilled in the art suitable for treating or preventing yeast or fungal, bacterial, viral and/or other microbial infections of plants, other substrates, animals and/or humans, or as can be found on or in any article of manufacture.

In certain embodiments, articles or products incorporating the compositions of the present invention can also include one or more preservative components known in the art, including but not limited to, sorbic or benzoic acid; the sodium, potassium, calcium and ammonium salts of benzoic, sorbic, hydroxymethyl glycinic, and propionic acid; and methyl, ethyl, propyl and butyl paraben and combinations thereof.

The compositions of this invention may contain a compound comprising an acidic or basic functional group and are, thus, capable of forming pharmaceutically- or otherwise-acceptable salts with pharmaceutically- or otherwise-acceptable acids and bases. The term "pharmaceutically-acceptable salts" refers to the relatively non-toxic, inorganic and organic acid and base addition salts of such compounds. Regardless, such salts can be prepared by reacting such a compound with a suitable acid or base. Suitable bases include the hydroxide, carbonate or bicarbonate of such an acceptable metal cation, ammonia, or such an acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. Representative acid addition salts include the hydrobromide, hydrochloride, sulfate, phosphate, nitrate, acetate, valerate, oleate, palmitate, stearate, laurate, benzoate, lactate, phosphate, tosylate, citrate, maleate, fumarate, succinate, tartrate, napthalate, mesylate, glucoheptonate, lactobionate, and laurylsulphonate salts and the like.

The compositions of the present invention can be used as aqueous dispersions or emulsions and are available in the form of a concentrate containing a high proportion of an FFC (with or without a surfactant) composition, as can be diluted (e.g., water or another fluid component) before use. Emulsifiable concentrates or emulsions may be prepared by dissolving a composition of the present invention, together with any other desired active ingredient, in a solvent optionally containing a wetting or emulsifying agent and then adding the mixture to water which may also contain a wetting or emulsifying agent. Suitable organic solvents include alcohols and glycol ethers. These concentrates should preferably be able to withstand storage for prolonged periods and after such storage be capable of dilution with water in order to form aqueous preparations which remain homogeneous for a sufficient time to enable them to be applied by conventional spray equipment.

Depending on the type of end-use application, articles or products incorporating compositions of the present invention may also comprise any other required components including, but not limited to, solid or liquid carriers to facilitate application, surfactants including biosurfactants, protective colloids, adhesives, thickeners, thixotropic agents, penetrating agents, stabilizers, sequestrants, texturing agents, flavoring agents (e.g., for post-harvest or processed food/beverage applications), sugars, colorants, etc., as will be well known to those skilled in the art.

For example, such compositions and/or related articles or products can be used for agricultural purposes and formulated with such a carrier or diluent. The compositions can be applied, formulated or unformulated, directly to the foliage of a plant, to seeds or to other medium in which plants are growing or are to be planted, or they can be sprayed on, dusted on or applied as a cream or paste formulation, or they can be applied as a vapor or as slow release granules. Application can be to, or proximate to, any part of the plant including the foliage, stems, branches or roots, or to soil surrounding the roots, fruit or vegetable (pre- or post-harvest) or to the seed before it is planted, or to the soil generally, to irrigation water or to hydroponic culture systems. The inventive compositions can also be injected into plants or sprayed onto vegetation (including fruits and vegetables) using low volume or pressure or electrodynamic spraying techniques, or any other treatment method known in the art or industry.

In certain embodiments, whether or not agricultural or related to food processing, compositions and/or articles or products impregnated with and/or incorporating compositions of this invention may be in the form of dustable powders or granules comprising a solid diluent or carrier, for example, fillers (also such as animal or cat litter), kaolin, bentonite, kieselguhr, dolomite, calcium carbonate, talc, powdered magnesia, fuller's earth, gypsum, diatomaceous earth, china clay and other impregnatable materials. Such granules can be preformed granules suitable for application without further treatment. These granules can be made either by impregnating pellets of filler with an inventive composition or another active ingredient or by pelleting a mixture of the active ingredient and powdered filler. For instance, compositions for dressing seed may include an agent (for example, a mineral oil) for assisting the adhesion of the composition to the seed; alternatively the active ingredient can be formulated for seed dressing purposes using an organic solvent. The compositions may also be in the form of wettable powders or water dispersible granules comprising wetting or dispersing agents to facilitate the dispersion in liquids. The powders and granules may also contain fillers and suspending agents. Alternatively, the compositions may be used in a micro-encapsulated form. They may also be formulated in biodegradable polymeric formulations to obtain a slow, controlled release of the active substance.

Regardless, such solid formulations comprising such an inventive composition can be provided in a range of products or articles in varying forms, shapes or moldings, including but not limited to cylinders, rods, blocks, capsules, tablets, pills, pellets (e.g., also pet foods), strips, spikes and the like. Alternatively, granulated or powdered material can be pressed into tablets or used to fill a range of capsules or shells. As discussed above, any such composition of this invention, whether formulated or unformulated, can be used alone, applied to a substrate or incorporated in a product or article of manufacture for a wide range of end-use applications, including but not limited to pharmaceutical, personal, industrial and agricultural compositions and related methods of use.

Generally, a useful solid carrier component can comprise any material that is at least somewhat porous and/or can hold an aforementioned antimicrobial composition without undue swelling. Together with materials of the sort described above and elsewhere herein, examples of such carrier components include silica gels, zeolites, calcium silicate, clays, activated charcoal, alumina, allophane, vermiculite, various absorbent and/or slow release polymers, and combinations thereof, as would be understood in the art by those made aware of this invention. In certain embodiments, such a carrier component can comprise one or more clay materials—examples of which useful in the context of this invention include, but are not limited to, attapulgite, montmorillonite, bentonite, hectorite, sericite and kaolin clays and mixtures thereof. Without limitation, bentonite clays, such as those comprising colloidal hydrated aluminum silicate containing varying quantities of iron, alkali and/or alkaline earth metals, have been found especially useful. Bentonite clay materials and related processed products are commercially available from a number of sources, including American Colloid Company of Arlington Heights, Illinois, under the trade name Bentonite AE H, together with other sources identified herein or as would be known to those skilled in the art.

Depending upon a particular article or end-use application, a volatile antimicrobial composition can be used neat or in combination with one or more solvents or diluent components, such as but not limited to water, aqueous alcohol and other solvents compatible with such an antimicrobial composition and/or an FFC component thereof. As a further consideration, the release or volatility of such an antimicrobial composition can be varied or adjusted by the presence of any one such solvent or diluent component.

Production of various articles of this invention generally involves admixture of an antimicrobial composition of this invention and a suitable solid carrier component. Admixture can be performed using any technique known in the art. As but one consideration, mixing technique and duration should be sufficient to disperse an antimicrobial composition over or throughout a solid carrier component. The order of admixture can vary. For instance, a solid carrier component can be provided or prepared, first, followed by addition of an antimicrobial composition. Alternatively, such an antimicrobial composition and all components used to produce a carrier component can be admixed together. With regard to the latter, the components can be admixed neat or with a solvent (e.g., water and/or an alcohol), dispersant or one or more other adjuvants. With respect to one formulation technique, the components used to produce a solid carrier and the antimicrobial composition can be admixed, with the latter, optionally, as an aqueous solution. In yet another embodiment, a powder form of a suitable carrier component can be admixed with an antimicrobial composition and a suitable binder component to provide an agglomeration of particles or granules of suitable dimension. Regardless of carrier identity, formulation technique or granule size, an antimicrobial composition can be present at about 1.0-about 3.0 wt. % of such an article and associated carrier component.

An article of this invention can be arranged and presented in conjunction with a package or enclosure for release or volatilization of an antimicrobial composition. A tote, lid, insert, covered tray or cup, carton, vial and other such enclosures known in the art can be used, providing sufficient article retention and antimicrobial release/vaporization therefrom. Examples of useful gas/vapor permeable enclosures include those configured in the shape of a flexible bag, pack or pouch of a mesh or non woven fabric composed of a gas permeable material.

The articles described herein are useful in affecting microbial activity, including inhibition of microbial growth, on and/or near a food item, thereby extending the shelf life of the food item. Toward that end, such an article—whether alone, without an enclosure or optionally presented in conjunction with a flexible bag or pouch—can be positioned with respect to or dropped in a container for shipping, storage or display of a desired food item (e.g., without limitation, fruits, vegetables and other agricultural produce), such container selected or designed depending on a particular food item. Article placement within such a container can be at any one or more points along a corresponding food supply and distribution chain.

EXAMPLES OF THE INVENTION

The following non-limiting examples and data illustrate various aspects and features relating to the compositions and/or methods of the present invention, including the preparation and use of antimicrobial compositions comprising various component compounds, as are described herein. In comparison with the prior art, the present compositions and methods provide results and data which are surprising, unexpected and contrary thereto. While the utility of this invention is illustrated through the use of several compositions and component compounds which can be used therewith, it will be understood by those skilled in the art that comparable results are obtainable with various other compositions and component compounds, as are commensurate with the scope of this invention.

Example 1a

Fungal Isolation. Several small stems of *Ananas ananassoides* were taken from a plant growing in the Bolivian Amazon in March of 2007. They were collected in a savanna region adjoining the rainforest at 12°40'07" S and 68°41'58" W and were immediately transported for analysis. Several small (2-5 inch) pieces from the stems were cut and placed into 70% ethanol for 30 seconds under a laminar flow hood. A pair of sterile tweezers was used to hold the stems separately in the flame to remove excess alcohol. Then small pieces of inner tissue (beneath the bark) were excised and placed onto potato dextrose agar (PDA) with an actively growing *M. albus* isolate 620 on one side of the plate having a center well removed from it. Effectively, this technique can be used to select for other isolates of *Muscodor* (Worapong et al., 2001a&b). During an incubation period of two weeks, the Petri plates were examined periodically for any fungal growth. Once hyphae were observed, the hyphal tips were aseptically cut out of the agar and placed on fresh PDA. The isolate was found in this manner. Several Petri plates (PDA) were used to determine if the fungus produced volatile antibiotics. This procedure included removing a 1-inch section of the agar from the middle of the plate, plating a plug of the isolate on one side and allowing it to grow for several days, and then plating test organisms on the other side of the gap.

Example 1b

Fungal Taxonomy. Fungus in nature is associated with *A. ananassoides* and is a deuteromycete belonging to mycelia sterilia. Fungal colonies whitish on all media tested when left out of direct sunlight. Fungal colonies pinkish on all media tested when put into direct sunlight. Spores or other fruiting bodies were not observed under any conditions. Hyphae (0.6-2.7 μm) commonly growing by branching, sometimes forming perfect coils (ca. 40 μm) and having cauliflower like bodies (3.5-14 μm) associated with them. Hyphae, newly developing, grow in an undulating pattern when observed under all conditions with all of the media tested. *Mycelium* on PDA covers the plate in 3-4 weeks and produces a fruity odor.

Holotype: Endophytic on *A. ananassoides*. Collections were made in the Bolivian Amazon in the Heath River area. The holotype comes from only one *A. annisoides* stem, collected in the Heath River country. A living culture is deposited as *Muscodor crispans* in the living Montana State University mycological collection as acquisition number 2347 (Feb. 29, 2008). Both 18S rDNA and ITS sequences of *M. crispans* (B-23) have been submitted to GenBank with the assigned serial number-EU195297.

Telomorph: The telomorph of this fungus may be found in Xylariaceae, based on the similarity of the 18S rDNA gene sequence data between *M. crispans* and the family Xylariaceae in the GenBank database (Bruns et al., 1991; Reynolds and Taylor 1993; Mitchell et al., 1995; Guano et al., 1999; Taylor et al., 1999). The molecular data from the 18S rDNA gene sequences of *M. crispans* show a 100% homology with *M. albus* isolate 620.

Etymology: The genus name, *Muscodor*, is taken from the Latin word which means musty. This is consistent with the quality of the odor produced by the first three isolates of the genus. The species name is *crispans*, from the Latin meaning "curly, wavy." The hyphae grow in regular undulating patterns.

Example 2a

Scanning Electron Microscopy. Scanning electron microscopy was performed on the isolate of example 1 after procedures described by Castillo et al. (2005). Agar pieces and host plant pieces supporting fungal growth were placed in filter paper packets then placed in 2% gluteraldehyde in 0.1 M sodium cacodylate buffer (pH 7.2-7.4) with Triton X 100, a wetting agent, aspirated for 5 minutes and left overnight. The next day the pieces were washed six×15-minute changes in water buffer 1:1, followed by a 15-minute change in 10% ethanol, a 15-minute change in 30% ethanol, a 15-minutes change in 50% ethanol, five×15-minute changes in 70% ethanol, and were then left overnight or longer in 70% ethanol. They were then rinsed six times for 15 minutes in 95% and then three 15-minute changes in 100% ethanol, followed by three 15-minute changes in acetone. The microbial material was critically point dried, gold sputtercoated, and images were recorded with an XL30

ESEM FEG in the high vacuum mode using the Everhart-Thornley detector. Hyphae were measured using Image J software available on-line.

Example 2b

Fungal Biology. The fungus produced a white mycelium on a water based medium. No fruiting structures or spores of any kind have been found under any lab conditions. Hyphae tend to intertwine to form coils. Other species of *Muscodor* also have this tendency (Worapong et al., 2001a). Newly developing hyphae tend to grow in an undulating fashion rather than the typical straight pattern and commonly intertwine to make rope like structures. This pattern of growth may prove useful as a diagnostic tool in identifying this organism in in-vivo inoculation studies. The fungus also produces cauliflower-like structures that seem to be connected to the hyphae by small strands. These bodies do not germinate under any conditions and thus appear not to be spores. This observation seems to be unique for *Muscodor* spp. and has not been noted as being present in any other fungal species in general.

Example 3a

Fungal Growth and Storage. It was determined that the isolate did not produce spores or any other fruiting bodies when several pieces of carnation leaves were placed on top of an actively growing isolate to encourage spore production, and no such structures were observed after a week of incubation at 23° C. The fungus was also plated on several different media including Cellulose Agar (CA), Malt Agar (MA), and Corn Meal Agar (CMA) to determine if spore production would be displayed. With the exception of a slower growth rate on some of the media, no other characteristics of the fungus appeared to be different, and no fruiting bodies or spores were observed.

Several methods were used to store the isolated fungus as a pure culture, one of which was the filter paper technique. The fungus was also allowed to grow on PDA, and then it was cut into small squares which were placed into vials containing 15% glycerol and stored at −70° C. The fungus was also stored at 4° C. by a similar method, using distilled water rather than glycerol. However, the most effective method of storage was on infested sterile barley seed at −70° C.

Example 3b

Figure 2:
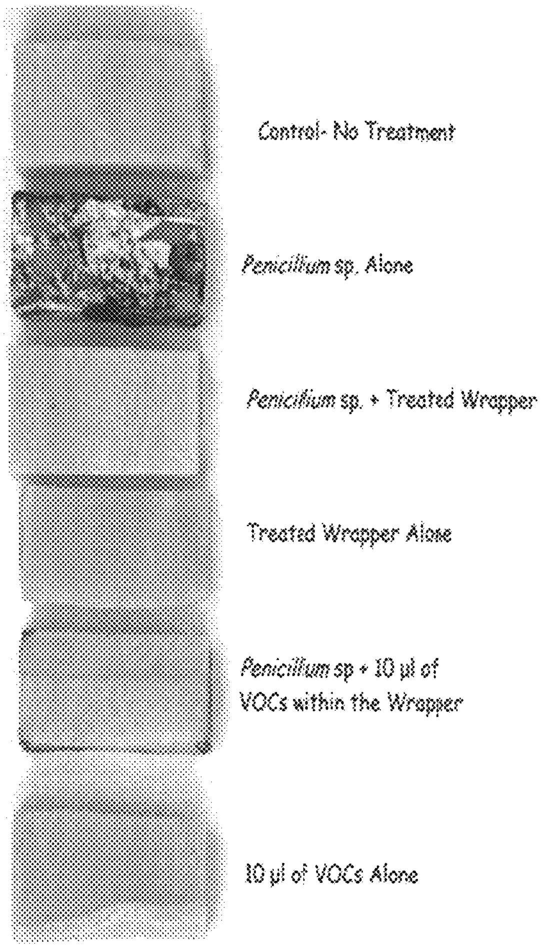
FIG. 2. A series of photographs illustrating the prevention of fungal growth (mold) on cheese by several methods employing the FFCs.
Figure 3:
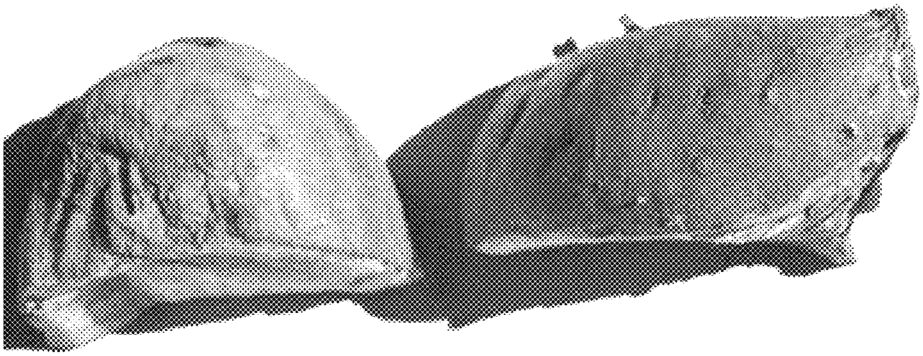
FIG. 3. The protective effect of the FFCs on yams in storage in the presence of 0.2 ml of an FFC composition for 2 days. The yams were then photographed after 10 days. (The test is on the left and the control is on the right.)

Other, more classical features of the isolated *M. crispans* were also examined and compared to *M. albus*. *Muscodor crispans* produced a slow growing, dense, white colored mycelium on all media tested, unless it was placed in direct sunlight, which caused the mycelium to develop a light pink color. This contrasts to *M. albus* that produces a whitish mycelium on all comparable media and conditions tested (Worapong et al., 2001a). The young hyphae also grew in an undulating fashion, rather than the characteristic straight cable-like fashion as commonly observed with *M. albus* (Strobel et al., 2001). No spores formed on any medium including ones containing the host plant material or carnation leaves. Hyphae varied in diameter (0.8-3.6 μm) and were often intertwined to make more complex structures and even hyphal coils (FIGS. 1-3). These hyphae were generally bigger than those of *M. albus* (Worapong et al., 2001a).

Example 4

Qualitative Analysis of Volatiles. The method used to analyze the gases in the air space above a 10-day old culture of the mycelium growing in Petri plates was comparable to that used on the original isolate of the *M. albus* strain cz-620 (Strobel et al., 2001). First, a baked "Solid Phase Micro Extraction" syringe (Supelco) consisting of 50/30 divinylbenzene/carburen on polydimethylsiloxane on a stable flex fiber was placed through a small hole drilled in the side of the Petri plate sporting the fungal growth. The fiber was exposed to the vapor phase of the fungus for 45 min. The syringe was then inserted into the splitless injection port of a Hewlett Packard 6890 gas chromatograph containing a 30 m×0.25 mm I.D. ZB Wax capillary column with a film thickness of 0.50 mm. The column was temperature programmed as follows: 30° C. for 2 min followed to 220° C. at 5° C./min. The carrier gas was ultra high purity Helium (local distributor), and the initial column head pressure was 50 kPa. Prior to trapping the volatiles, the fiber was conditioned at 240° C. for 20 minutes under a flow of helium gas. A 30 second injection time was used to introduce the sample fiber into the GC. The gas chromatograph was interfaced to a Hewlett Packard 5973 mass selective detector (mass spectrometer) operating at unit resolution. Data acquisition and data processing were performed on the Hewlett Packard ChemStation software system. Initial identification of compounds in the volatile mixture produced by the fungus was made through library comparison using the NIST database.

Example 5a

Fungal DNA Isolation and Acquiring ITS-5.8S rDNA Sequence Information. A 10 day old culture of the present fungus, growing on PDA, was used as a source of DNA after incubation at 25° C. using the Rapid Homogenization: Plant leaf DNA Amplification Kit (Cartagen; Wash., USA). Some of the techniques used were comparable to those used to genetically characterize other *M. albus* isolates from Australia (Ezra et al., 2004). Squares of the cultured mycelia (0.5 $cm^2$) were cut from one week old cultures. The agar was scraped from the bottom of the pieces, in order to exclude as much agar as possible. The pieces were placed into 1.5 ml Eppendorf vials and incubated for about 10 minutes at −80° C. The DNA was then extracted according to the instructions of the kit manufacturer. Extracted DNA was diluted (1:9) in double-distilled, sterile water and 1 μl samples were used for PCR amplification. The ITS1, 5.8S ITS2 rDNA sequence was amplified by the polymerase chain reaction using the primers ITS1 (TCCGTAGGTGAACCTGCGGG) (SEQ ID NO: 1) and ITS4 (TCCTCCGCTTATTGATATGC) (SEQ ID NO: 2). The PCR procedure was carried out in a 14 μl reaction mix containing 1 μl DNA extracted from the fungal culture (1:9 dilution), 0.5 μl primer ITS1 and 0.5 μl primer ITS4, 7 μl RedMix™ plus PCR mix with 1.5 mM $MgCl_2$ (GeneChoice, Inc., Maryland, USA) and 5 μl $ddH_2O$ PCR grade (Fisher Scientific, Wembley, Western Australia, Australia). The PCR amplification was performed in a Biometra personal cycler (Goettingen, Germany): 96° C. for 5 minutes followed by 35 cycles of 95° C. for 45 seconds, 50° C. for 45 seconds and 72° C. for 45 seconds, followed by a 72° C. cycle for 5 minutes. The PCR products were examined using gel electrophoresis, on a 1.3% agarose gel for 30 minutes at 100V with TAE buffer (GelXLUltra V-2 from Labnet International, Inc., (Woodbridge, NJ, USA) or Wealtec GES cell system, from (Wealtec Inc., Georgia, USA). Gels were soaked in a 0.5 μg ml-1 ethidium bromide solution for 5 minutes and then washed in distilled water for 5 minutes. Gel imaging was performed under UV light in a Bio-Imaging System (model 202D; DNR-Imaging Systems, Kiryat Anavim, Israel). A ~500 bp PCR product was purified using the UltraClean PCR Clean Up DNA Purification Kit (MO BIO Laboratories, Inc., California, USA). Purified products were sent for direct PCR sequencing. Sequencing was performed on both strands of the PCR product using ITS1 and ITS4 primers. Sequencing was performed using DYEnamic ET terminators on a MegaBACE™ 1000 analysis system (Danyel Biotech Ltd., Rehovot, Israel). Sequences were submitted to the GenBank on the NCBI web site. Sequences obtained in this study were compared to the GenBank database using the BLAST software on the NCBI web site.

Example 5b

Molecular Biology of *Muscodor crispans*. The partial sequences of 18S rDNA, ITS1, 5.8S, and ITS2 have been demonstrated to be highly conserved regions of DNA and therefore very useful in the classification of organisms (Mitchell et al., 1995). These molecularly distinguishing partial sequences of *M. crispans* were obtained and compared with the data in GenBank. After searching the 18S rDNA sequences, 525 bp of *M. crispans* were subjected to an advanced BLAST search. The results showed 100% identity with 525 bp of *M. albus* (AF324337). Comparative analysis of the partial ITS 1&2 and 5.8S rDNA sequences of *M. crispans* hit ITS 1 and 2 of *M. albus* (AF324336), *M. roseus* (AY034664), *X. enteroleuca* CBS 651.89 (AF163033), *X. arbuscula* CBS 452.63 (AF163029), and *Hypoxylon fragiform* (HFR246218) at 95, 95, 90, 90, and 91% homologies, respectively.

Example 5c

While this invention is, in part, described in conjunction with isolated novel fungi, it will be understood that variants and mutants of such fungi—as would be understood in the art—are also contemplated in the context of the present invention. The terms "variant" and "mutant" can be defined as provided in U.S. Pat. No. 6,911,338, the entirety of which is incorporated herein by reference. Accordingly, this invention can be directed to variant or mutant strains of *M. crispans* and corresponding compositions thereof.

Example 6a

Bioassay tests for *M. crispans* against plant pathogens. The vapor of the volatile by-product of *M. crispans* was tested for microbial inhibitory activity using a relatively simple test, as previously described in the literature (Strobel, et al., 2001). A strip of agar (2 cm wide) in a standard PDA Petri dish was removed and *M. crispans* was inoculated and allowed to grow on one side of the plate for about a week. The test fungus or bacterium was then inoculated on the other side of the Petri dish, using small plugs of agar for the fungi. The bacteria and yeasts were streaked onto the agar (1.5 cm long). The plate was then wrapped with one piece of Parafilm and incubated at 23° C. for 48 hr. The effect of *M. crispans* on the growth of the test organisms and determined first by verifying the presence or absence of growth where the inoculations had taken place. If growth was observed, measurements of the diameter in two locations of the fungal hyphae were taken. The biological activity of the vapor on bacteria and yeasts were assessed by estimating the degree to which their growth was affected as percentage of growth on a control plate (Strobel et al., 2001). If no growth was observed, the test organism was aseptically removed from the test plate and inoculated onto a fresh PDA plate at some time point after exposure to the vapor in order to ascertain viability of the test organism.

Utilizing the preceding methodology, when *M. crispans* was grown for 7-10 days at 23° C. on PDA, the volatile by-product of the fungus proved to be lethal to several fungi and bacteria. Gram-negative and Gram-positive bacteria, as well as yeasts and each of the major classes of fungi, were utilized as test organisms. Most of the test organisms were 100% inhibited and died after a 2 day exposure to the by-product of *M. crispans*. (See Table 8.) Some of the test organisms did not succumb to the volatiles of *M. crispans* after a two day exposure, but their growth was significantly inhibited by the volatile by-product, and they were killed after a four day exposure. Such organisms include *Penicillium roquefortii, Bipolaris sorokiniana, Stagonospora* sp., and *Fusarium oxysporum*, among others.

TABLE 8

Effects of the *M. crispans* volatile by-product on many fungal pathogens of plants and some assorted bacteria. The inhibition values were calculated as % of growth inhibition as compared to an untreated control test organism. The tests were repeated at least 3 times with comparable results. Inhibition of the test organisms was recorded 48 hours after exposure to the fungus and vapor of the volatile fungal by-product.

| Test organism | Inhibition (%) after 48 hours exposure | Alive after 48 hours exposure | Alive after 96 hours exposure |
|---|---|---|---|
| *Alternaria helianthi* | 100 | N | N |
| *Aspergillus fumigatus* | 100 | Y | N |
| *Bacillus subtilis** | 100 | N | N |
| *Bipolaris sorokiniana* | 100 | Y | N |
| *Botrytis cinerea* | 100 | N | N |
| *Candida albicans** | 100 | N | N |
| *Cephalosporium gramineum* | 100 | N | N |
| *Ceratocystis ulmi* | 100 | Y | N |
| *Cochiolobolus carbonum* | 100 | N | N |
| *Colletotrichum lagenarium* | 100 | N | N |
| *Curvularia lunata* | 100 | Y | N |
| *Drechslera teres* | 100 | N | N |
| *Drechslera tritici-repentis* | 100 | N | N |
| *Dreschlera portulacae* | 100 | N | N |
| *Escherichia coli** | 100 | N | N |
| *Fusarium avenaceum* | 100 | N | N |
| *Fusarium culmorum* | 100 | N | N |
| *Fusarium oxysporum* | 100 | Y | N |
| *Fusarium solani* | 50 | Y | Y |
| *Ganoderma* sp. | 100 | Y | N |
| *Geotrichum candidum* | 100 | Y | N |
| *Mycosphaerella fijiensis* | 100 | N | N |
| *Penicillium roquefortii* | 100 | Y | N |
| *Phytophthora cinnamomi* | 100 | N | N |
| *Phytophthora palmivora* | 100 | N | N |
| *Pythium ultimum* | 100 | N | N |
| *Rhizoctonia solani* | 100 | N | N |
| *Saccharomyces cerevisiae** | 90-95 | N | N |
| *Sclerotinia sclerotiorum* | 100 | N | N |
| *Stagonospora* sp. | 100 | Y | N |
| *Tapesia yallundae* | 100 | N | N |
| *Trichoderma viridae* | 10 | Y | Y |
| *Verticillium dahliae* | 100 | Y | N |
| *Xanthomonas axonipodis* p.v. *citri** | 100 | N | N |

*Denotes that these organisms were streaked onto the test plate, and an indication of growth was made if colony development eventually occurred. After appropriate exposure to the volatile by-product of *M. crispans*, the streaked area was compared to the growth on the control plate and estimated for the % inhibition. Eventually each organism was restreaked on to a PDA plate to test for viability.

Example 6b

With reference to Table 8, the effect of the vapor of the volatile by-product of *M. crispans* on *Botrytis* is quite noticeable—especially on *B. cinerea*, the cause of gray mold of various plants. The inhibitory and killing effects are also applicable to *Botrytis allii* which causes gray mold neck rot of onion. Without limitation, such results suggest the present invention can be used effectively to modify the produce surface or storage atmosphere post-harvest to prevent mold and related issues. Likewise, such results support use of an FFC composition of this invention to treat onion (e.g., Vidalia onions), shallot and garlic produce to prevent or control fungal growth.

Example 6c

Vapor from the volatiles of *M. crispans* are also effective against many of the fungi causing decay and fungal growth on grain (e.g., corn, wheat, barley, rice, etc.), and this invention can be used in conjunction with various fruits and vegetables such as potatoes, beets, carrots sweet potatoes—such grains, fruits or vegetables, whether before or after harvest, in storage or shipment. Accordingly, the compositions and methods of this invention can be applied to some of the major fungi-related issues in the agriculture and food processing fields, and can be used to target organisms such as but not limited to *Alternaria, Cladosporium, Aspergillus, Penicillium, Diplodia, Fusarium* and *Gibberella*. (See, e.g., Table 8.)

Example 6d

Vapor from the by-product of *M. crispans* was effective against the *Mycosphaerella fijiensis* fungus. (See, Table 8.) Accordingly, the invention can be used as treatment for the fungus-associated Black Sigatoka disease of bananas and plantains.

Example 6e

Citrus canker disease threatens the very existence of the United States citrus industry. As shown in Table 8, vapor from the by-product of *M. crispans* effectively kills the canker-causing pathogen *Xanthomonas axompodis* p.v. citri. Such results suggest that FFC compositions and related methods of the present invention can be used effectively to treat seeds, seedlings, orchards, equipment or apparatus (including, e.g., worker equipment and clothing) and/or harvested fruit to prevent, inhibit or control canker disease.

Example 7

As a follow up to the tests and results of Example 6, bioassay tests with the vapor of the volatile by-product of M. cri spans were run against various other plant and human pathogenic fungi and bacteria. (See, Table 9, below). The fungus was grown on X-plates with PDA in one quadrant and incubated for 3-5 days at room temperature prior to inoculation with one or more test organisms. Control plates were made at the same time of inoculation and grown on the same medium that was optimal for the individual test organism. The test organisms, *Staphylococcus aureus* 6538, *Salmonella cholerasuis* 10708, *Escherichia coli* 11229, *S. aureus* ATCC 43300 (MRSA), and *Vibrio cholerae* ATCC 14035, were grown on Trypticase Soy Agar (TSA) in the three remaining quadrants of the X plate. Three plates of each organism, with appropriate controls, were exposed to the vapor of the by-product of the fungus for approximately two, four and six days at room temperature. In order to check for the viability of the test microbe, the fungus was then physically removed, and the control and test plates were placed in an incubator at 35±1° C. for a minimum of three to four days, with the exception of the *Mycobacterium* spp. which were incubated for approximately one additional month. This was done in order to ascertain if the vapor of the by-product had inhibited or killed the test organism, and viability of the organism was assessed. This same protocol was followed for the *Yersinia pestis* and *Bacillus anthracis*, except that the exposure times were changed to 3 and 5 days, and *Y. pestis* was incubated at 28±1° C. and in 5% $CO_2$ after exposure to the fungus. The *Mycobacterium marinum* ATCC 927 was grown on 7H11 agar (Difco Co) in the remaining three quadrants, using the previously stated protocol, and incubated at 33±1° C. All three replicates in the tests with each organism behaved identically.

For all *Mycobacterium tuberculosis* strains, also grown on 7H11, a section of agar was removed from the plate and the B-23 fungus (on PDA) was inserted. The plates were then inoculated from a broth culture. Control plates, where no fungus was present, were also inoculated. At each appointed time interval, a section of agar was removed from the plates and transferred to a separate and empty plate and placed in an incubator at 35±1° C. in order to determine the viability of the microbe. The plates were placed in a plastic bag with moistened paper towels to prevent desiccation.

*Pseudomonas aeruginosa* 15442 and *Burkholderia thailandensis* 70038 were both grown on TSA agar. They were left at room temperature for the optimal growth time for the organism and then moved to an incubator at 35±1° C. and observed. It is to be noted that all tests using human pathogens were conducted under strict and federally approved biosafety conditions. All tests on human pathogens were repeated at least twice.

TABLE 9

Effects of the volatile by-product of *M. crispans* on various Gram+ and Gram− bacterial species. The exposure times were varied according to the particular organism of interest, and the viability of the test organism was determined after that period (listed as growth or no growth).

| Organism | Type of Cell Wall | Exposure Time | Growth/No Growth (in the presence of *M. crispans*) | Comments |
|---|---|---|---|---|
| *S. aureus* 6538 | Gram+ | 2, 4 and 6 days | No growth | |
| *S. cholerasuis* 10708 | Gram− | 2, 4 and 6 days | No growth | |
| *P. aeruginosa* 15442 | Gram− | 2 days | Growth | No visible difference between exposed and control plates. |
| *M. marinum* ATCC 927 | Acid-fast | 2, 4 and 6 days | No growth | |
| *B. thailandensis* 70038 | Gram− | 2 days | Growth | No visible difference between exposed and control plates. |

TABLE 9-continued

Effects of the volatile by-product of *M. crispans* on various Gram+ and Gram− bacterial species. The exposure times were varied according to the particular organism of interest, and the viability of the test organism was determined after that period (listed as growth or no growth).

| Organism | Type of Cell Wall | Exposure Time | Growth/No Growth (in the presence of *M. crispans*) | Comments |
|---|---|---|---|---|
| *S. aureus* ATCC 43300 (MRSA) | Gram+ | 2, 4 and 6 days | Growth | No actual colonies formed, just a slightly filmy growth. |
| *E. coli* 11229 | Gram− | 2, 4 and 6 days | Growth | No visible difference between exposed and control plates. |
| *V. cholerae* ATCC 14035 | Gram− | 2, 4 and 6 days | Growth | Growth at 4 and 6 day exposures appears to be slightly inhibited in comparison to control plates. |
| *Y. pestis* 91-3365 | Gram− | 3 and 5 days | No growth | |
| *B. anthracis* A2084 | Gram+ | 3 and 5 days | Growth | Only a few colonies left after exposure and when incubated, more grew. |
| M. tuberculosis 3081 (resistant to isoniazid) | Acid-fast | 2, 4, 7 and 14 days | No growth | |
| *M. tuberculosis* 50001106 (resistant to streptomycin) | Acid-fast | 2, 4, 7 and 14 days | No growth | |
| *M. tuberculosis* 59501228 (resistant to streptomycin/ethambutol) | Acid-fast | 2, 4, 7 and 14 days | No growth | |
| *M. tuberculosis* 59501867 (susceptible) | Acid-fast | 2, 4, 7 and 14 days | No growth | |

As shown in Table 9, all four acid-fast bacteria (*Mycobacterium tuberculosis* strains) were killed after 2, 4, 7, and 14 day exposure to actively growing *M. crispans* (6-10 day old culture). Other bacteria which were killed after at least 2 days of exposure to *M. crispans* were: *Staphylococcus aureus* 6538, *Mycobacterium marinum, Yersinia pestis*, and *Salmonella choleraesuis*. Relatively somewhat or completely unaffected by exposure to *M. crispans* were the following: *Pseudomonas aeruginosa, Burkholderia thailandensis, Staphylococcus aureus* (MRSA), *Escherichia coli, Vibrio cholera*, and *Bacillus anthracis*. However, the growth of *S. aureus* (MRSA) was only a slimy film rather than any distinct colonies and thus it was affected by the VOCs of *M. crispans*. In addition, the *B. anthracis* plate had only a few colonies left on the exposure plate, but more colonies grew after removal of *M. crispans* and subsequent incubation. Therefore, it is suspected that *M. crispans* vapor of the by-product is only effective against the vegetative cells of *B. anthracis*, but not against the spores. One month after the last observation time (14 days), no growth was observed on any of the plates exposed to the fungus, and growth was observed on all of the control plates.

The experiments of the following examples illustrate various embodiments of the inventive compositions and the utility thereof. One representative composition, without limitation as to component amount, concentration or ratio, is provided in Table 10. In certain embodiments, an amount of isobutryic acid can be replaced with propanoic acid at or about the same level. In certain such or other embodiments, ethanol can be replaced with acetic acid and/or 2-butanone can be replaced with either acetic acid or propanoic acid. Also, various esters can be replaced with isomers or homologs (e.g., without limitation, a 3-methylbutyl ester, of propanoic acid, for a 2-methylbutyl ester thereof) of the esters listed. The results observed in the following examples were obtained with a composition of the compounds listed in Table 10. Consistent therewith, various other compositions can be used with comparable effect.

TABLE 10

| A composition of food and flavor compounds useful in the control of harmful microorganisms. Compound* in a Series of FFCs |
|---|
| Acetaldehyde |
| Ethyl Acetate |
| 2-Butanone |
| Propanoic acid, 2-methyl-, methyl ester |
| Ethanol |
| Acetic acid, 2-methylpropyl ester |
| Propanoic acid, 2-methyl-, 2-methylpropyl ester |
| 1-Propanol, 2-methyl- |
| 1-Butanol, 3-methyl-, acetate |
| Propanoic acid, 2-methyl-, 2-methylbutyl ester |
| 1-Butanol, 3-methyl- |
| Propanoic acid, 2-methyl- |
| Acetic acid, 2-phenylethyl ester |

*Each of these compounds occurs as a liquid at room temperature and can be used one with another to provide a liquid composition that readily volatilizes at room temperatures or temperatures and pressures that otherwise permit volatilization.

An FFC Composition Used for Plant Disease Control.

Example 8a

The relative ability of the FFCs to inhibit and kill test organisms was measured. Test solutions were prepared by placing compounds in vials, in the relative proportions given in Table 10. The test mixture (20 microliters) was placed in a presterilized microcup (4×6 mm) located in the center of a Petri plate containing PDA. When not in use, the mixture was stored at 0° C. The test organisms (as mentioned in Table 9), freshly growing and excised on 3 $mm^3$ agar blocks (at least 3 agar blocks per test fungus), were placed 2-3 cm from the microcup and the plate wrapped with two layers of parafilm. Measurements were made on mycelial growth from the edge of the agar blocks after a given time period. However, in the case of *Geotrichum candidum* they were streaked and checked for new visible growth and viability by restreaking from the original area of the agar plate that had been inoculated. Appropriate controls were also set up in which no test solution was placed into the microcup. Tests on 20 μl of the FFC mixture were done at least twice with comparable results.

Example 8b

Viability of the test microbes was made by aseptically removing the small agar block and placing it on a PDA plate and observing growth after 1-3 days, or by re-streaking the *Geotrichum candidum* on a fresh PDA plate. In this manner the viability of the microbes could be assessed. The results shown in Table 11a indicate that the organisms listed below are all inhibited by the particular FFC composition and in most cases killed by the exposure to them. These include *Aspergillus niger, Penicillium* sp. on cheese, *Cercospora beticola, Verticillum dahaliae, Pythium ultimum, Phytophthora palmivora, Mycophaeraella fifiensis, T Rhizoctonia solani, Aspergillus fumigatus, Geotrichum candidum Trichoderma viridi, Ganoderma* sp., *Curvularia* sp., and *Botrytis alli*. Thus, when properly applied, an FFC composition has an ability to control these pathogenic microbes. Such results indicate many other pathogenic microbes can be either inhibited or killed by this mixture.

Table 11a. A brief list of various plant pathogenic microbes and their sensitivities to a representative FFC composition of this invention, with an exposure to 20 microliters of the mixture for 2 days at 23° C. on potato dextrose agar (PDA) in a parafilm sealed Petri plate. The agar plugs with the test microbe were eventually tested for viability after removal and placement on a regular Petri plate of PDA.

TABLE 11a

A brief list of various plant pathogenic microbes and their sensitivities to a representative FFC composition of this invention, with an exposure to 20 microliters of the mixture for 2 days at 23° C. on potato dextrose agar (PDA) in a parafilm sealed Petri plate. The agar plugs with the test microbe were eventually tested for viability after removal and placement on a regular Petri plate of PDA.

| Test Organism | Effect on Growth | Alive or Dead after 48 hr |
|---|---|---|
| *Aspergillus niger* | No growth | Dead |
| *Penicillium* sp. on cheese | 95% inhibition | Alive |
| *Cercospora beticola* | No growth | Dead |
| *Verticillum dahaliae* | No growth | Dead |
| *Pythium ultimum* | No growth | Dead |
| *Phytophthora palmivora* | No growth | Dead |
| *Mycophaeraella fijiensis* | No growth | Dead |
| *Rhizoctonia solani* | No growth | Dead |
| *Aspergillus fumigatus* | No growth | Dead |
| *Geotrichum candidum* | No inhibition | Alive |
| *Trichoderma viridi* | 60% inhibition | Alive |
| *Ganoderma* sp | No growth | Dead |
| *Curvularia* sp | No growth | Alive |
| *Botrytis alli* | No growth | Dead |

Example 8c

With reference to the data of Table 11a, the activity profile of the FFC composition utilized indicates, in several instances, different and/or enhanced antimicrobial effect, as compared to *M. crispans* and vapors of the volatile by-product thereof.

Example 8d

With reference to the preceding example and using comparable techniques and procedures, the same pathogens were treated with propanoic acid vapors. Comparative results are shown in Table 11b, below, with the data of Table 11a reproduced in columns A and B, and observed effects of propanoic acid, alone, provided in column C (% inhibition). At 20 μl the amount of propanoic acid is comparable to a level of propanoic acid in certain embodiments of this invention. Propanoic acid is representative of various lone compounds of the prior art known to have certain antimicrobial effect. However, as demonstrated by comparative data of Table 11b, the present compositions provide new and synergistic results over and beyond that expected independently from a lone prior art component outside the context of this invention. As shown therein, while the prior art is at best merely inhibitory, the inventive compositions eliminate (i.e., kill) many pathogens tested. Similar results are obtainable by comparison with other such lone prior art compounds/compositions.

TABLE 11b

Comparative results showing improved antimicrobial activity over propanoic acid.

| Test Organism | Effect on Growth (A) | Alive or Dead after 48 hr (B) | Propanoic Acid alone at 20 μl After 24 hr (C) |
|---|---|---|---|
| *Aspergillus niger* | No growth | Dead | 0% Alive |
| *Penicillium* sp. on cheese | 95% inhibition | Alive | |
| *Cercospora beticola* | No growth | Dead | 75% Alive |
| *Verticillum dahaliae* | No growth | Dead | |
| *Pythium ultimum* | No growth | Dead | 80% Alive |
| *Phytophthora palmivora* | No growth | Dead | 100% ND* |
| *Mycophaeraella fijiensis* | No growth | Dead | |
| *Rhizoctonia solani* | No growth | Dead | 80% Alive |
| *Aspergillus fumigatus* | No growth | Dead | 0% Alive |
| *Geotrichum candidum* | No inhibition | Alive | 0% Alive |
| *Trichoderma viridi* | 60% inhibition | Alive | |
| *Ganoderma* sp | No growth | Dead | |
| *Curvularia* sp | No growth | Alive | |
| *Botrytis alli* | No growth | Dead | 0% Alive |

*100% inhibition, but viability not determined (ND).

Use of FFC Compositions for Treating Tuberculosis and Other Human Pathogens

Example 9a

Four clinical drug resistant strains of *M. tuberculosis* isolates (5901867, 50001106, 59501228 and 3081) were exposed to an FFC composition. For each isolate, 10 μL of the culture was placed in the middle of a 7H11 agar plate and then evenly spread across the whole surface of the plate with a sterile plastic loop. Lids from 0.65 ml microcentrifuge tubes (micro caps) were cut off and autoclaved at 121° C. for 15 minutes inside an autoclavable tube with a screw-cap lid. Sterile forceps were used to remove a micro cap which was placed in the center of the inoculated plate. The control plates (one for each isolate) did not receive a micro cap. Three plates for each isolate were made and 5, 10, or 20 μL of the FFCs were placed in each of the three micro caps of the respective plates. The plates were then placed into a zip-lock sealed plastic bag with a damp paper towel and incubated at 36° C.±1° C. for approximately 28 days. After approximately 48 hours of exposure, the micro cap was removed and disposed of and the plates were returned to the incubator. The paper towels were frequently checked and re-moistened to prevent dehydration of the media. All of the control plates had growth. All of the plates that were exposed to 5 and 10 μL of volatiles had growth. Only one isolate (50001106) exposed to 20 μL of volatiles had growth. It is to be noted that each isolate of *M. tuberculosis* is a clinical drug resistant strain of this organism. All experiments were carried out in US Government Approved Biosafety Laboratory Conditions.

The control plates and the plates exposed to 5 and 10 μL of volatiles were plated on Apr. 14, 2008. The plates exposed to 20 μL of volatiles were plated on Apr. 22, 2008. All plates were checked multiple times. The final check was performed on May 19, 2008 and those organisms that did not survive are indicated on the Table 12 as "--."

TABLE 12

Inhibitory Effects of the FFCs in the growth of drug resistant *M. tuberculosis*

| Isolate of *M. tuberculosis* | 5 μL | 10 μL | 20 μL |
|---|---|---|---|
| 5901867 | + | + | — |
| 50001106 | + | + | + |
| 59501228 | + | + | — |
| 3081 | + | + | — |

The actual effects of an FFC composition of this invention on another strain of TB are shown in FIG. 1: The killing effect of the FFCs on a strain (110107) of *M. tuberculosis*. The plate on the left is a control plate that had not been treated with 20 microliters of the FFCs for 48 hours, while the plate on the right was treated for 48 hours both plates were then incubated for 28 days at 36° C. It is obvious from these experiments that the FFCs were able to kill % of the drug resistant isolates of *M. tuberculosis*. The prospect now exists for animal and eventually human trials using such FFC compositions in the treatment of tuberculosis.

Example 9b

Consistent with the data of the preceding example, broader aspects of this invention can be demonstrated. Viable cultures and suitable media are prepared using materials and techniques well-known to those skilled in the art. For instance, exposure to an FFC composition of this invention (e.g., by direct contact of a liquid composition or by vapors therefrom) can result in growth inhibition or death of the following coliform bacteria (gram stain and morphology): *Escherichia coli* (gram negative, rod), *Salmonella enteritidis* (gram negative, rod), *Pseudomonas aeruginosa* (gram negative, rod), *Staphylococcus aureus* (gram positive, cocci) and *Listeria monocytogenes* (gram positive, rod).

Likewise, such results can also be obtained and demonstrated with various other gram-negative and/or gram-positive bacteria such as but not limited to *Bacillus cereus* (gram positive, rod) and *Clostridium botulinum* (gram positive, rod).

Example 10

The $IC_{50}$ was calculated for some of the test organisms that were tested against an artificial composition to mimic the volatile by-product of *M. crispans*. (See, Table 1.) With reference to Table 12, all of the test organisms were inhibited 100% with the utilization of 15 μL of the artificial mixture, and several of them were killed with as little as 10 μL. *Verticillium dahliae, Botrytis cinerea*, and *Aspergillus fumigatus* were not killed by even the largest volume of the mixture (30 μL), but all three were 100% inhibited with 10 or 15 μL of the test mixture. The most sensitive organism was *Pythium ultimum*, which was killed with 10 μL and 100% inhibited with 2.5 μL thus it is the case that the $IC_{50}$ values do not necessarily reflect the killing ability of the volatiles since both *P. ultimum* and *Botrytis cinerea* possess virtually the same $IC_{50S}$ but one is killed and the other was not (Table 13).

TABLE 13

The $IC_{50}$s of the artificial mixture of the components of the volatile by-product of *M. crispans* on various plant pathogens. Amounts of the mixture, ranging from 1 μL to 30 μL, were added to a sterile plastic well in the center of the test plate, and the pathogenic organisms were placed around the edge of the plate. Viability was assessed after 48 hours and compared to a control plate with no mixture added but with the sterile well in place. Any organisms which showed no growth after that period were determined to be 100% inhibited, while those which showed no growth after the 48 hours and no growth after isolation onto PDA immediately following the 48 hour assessment were considered dead. The $IC_{50}$ calculation was determined by dividing the amount of the artificial mixture required to cause 50% inhibition (in μL) by the total air space in the Petri dish (50 mL).

| Test Organism | Minimum volume to cause 100% inhibition (μL) | Volume to cause death (μL) | IC 50 ($\mu L\ mL^{-1}$) |
|---|---|---|---|
| *Pythium ultimum* | 2.0 | 10.0 | 0.030 ± 0.004 |
| *Phytophthora cinnamomi* | 5.0 | 30.0 | 0.056 ± 0.009 |
| *Sclerotinia sclerotiorum* | n/a | >30 | 0.15 ± 0.016 |
| *Botrytis cinerea* | 10.0 | >30 | 0.035 ± 0.004 |
| *Rhizoctonia solani* | 20.0 | 15.0 | 0.039 ± 0.006 |
| *Aspergillus fumigatus* | 2.0 | 20 | 0.031 ± 0.003 |
| *Verticillium dahliae* | 5.0 | >30 | 0.062 ± 0.004 |
| *Phytophthora palmivora* | 1.0 | 5.0 | <0.02 |

Use of an FFC Composition for the Treatment of Garbage to Control Microbial Decay Example 11

Figure 4:
FIG. 4. The protective effect of the FFCs from the decay of garbage for 10 days held at 30° C.

An artificial mixture of items, which would normally be considered as garbage, was assembled into two ammo cartridge boxes. These items consisted of waste cereal items, flower parts, meat wastes, newspaper fiber, and miscellaneous other wastes. Into one box was placed a small beaker containing 0.2 ml of the aforementioned FFC composition. Into the other box was placed a beaker with no FFCs. Both boxes were incubated for 10 days at 80° F. At the end of that time the boxes were opened and examined. It was obvious that no decay had occurred in the box with the FFCs. On the other hand, the control box had completed turned to a massive amount of decay. The use of the FFC composition for garbage treatment is an opportunity to save intact garbage form decay whilst in transit to facilities around the world that ferment the garbage into energy related products such as methane. FIG. 4 illustrates that the FFC composition protected the garbage from microbial decay under the conditions of this experiment.

Use of an FFC Composition for the Treatment of Cheese to Control Fungal Decay

Example 12

A vial containing 10 ml of the aforementioned FFC composition was incorporated in or with and/or used to soak a piece of clear plastic Saran® wrap 10×10 inches. The plastic wrap was soaked in the FFC composition for 6 days, dripped dried and then used as a wrapper over the cheese piece thoroughly inoculated with a cheese strain of *Penicillum* sp. In another experiment, the cheese piece was inoculated with the fungus then wrapped with regular Saran® wrap and then injected with 10 microliters of the FFCs. The appropriate controls are indicated on the illustration above with *Penicillium* sp. alone, treated wrapper alone, the FFCs alone and control (no treatment). The experimental cheese pieces were incubated for 1 week at room temperature and then portions of each cheese item was eat-tested by lab personnel. It is to be noted that there was no adverse effects of storage in this manner with a prostitution of the taste of the cheese when compared to a newly cut fresh piece of cheese that had been stored in the refrigerator. The totally fungal infested cheese piece was not eaten. It is obvious from FIG. 2 that use of an FFC composition under the wrapper or with the treated wrapper caused virtually complete protection of the cheese piece from decay and colonization of the cheese by *Penicillum* sp. This was true with the treated wrapper and with the injection of 10 microliters of FFCs under the plain Saran wrapped cheese alone.

Use of an FFC Composition for the Treatment of Food and Plant Parts (e.g., plant produce) to Control Fungal Decay Example 13a Several yams were obtained for these experiments. It was thought that the surface contaminating microbes causing eventual decay would be plentiful enough for the inoculum. Thus, two yam pieces were placed in a plastic box with the lid sealed in the presence of a small beaker containing 0.2 ml of the FFCs. The control box contained a beaker with no FFCs. The sealed boxes were then held at room temperature for 10 days and then examined. It was obvious that no surface and deeper contamination of the treated yam pieces developed, while the control yams developed multiple areas of surface blemishes and insipient decay as illustrated in FIG. 3: The untreated yam is on the left and the one on the right has been treated with the FFCs. Note the large area of fungal decay on the top end of the yam on the left.

Example 13b

As a related end-use application, an FFC composition and/or component thereof can be applied to harvested fruit or vegetable produce to compensate for removal of any natural, waxy or protective coating thereon. For instance, harvested squash and similar produce, with cut stems, can be treated with an FFC composition (e.g., with spray application) to control/inhibit microbial growth, improve marketability and extend shelf life.

Example 14

A synthetic FFC composition of this invention, in accordance with compositions of the sort described in Tables 2-7 and 10, compared favorably with the use of live *M. albus* for control of seedling diseases of sugar beet (*Beta vulgaris* L.) caused by *Pythium ultimum, Rhizoctonia solani* AG 2-2 and *Aphanomyces cochlioides*, and root knot nematode, *Meloidogyne incognita*, on tomato (*Lycopersicon esculentum*). The synthetic composition provided control of damping-off equal to a starch-based formulation of the live fungus for all three sugar beet pathogens, and significantly reduced the number of root-knot galls on tomato roots. Rate studies with the FFC composition utilized showed that concentrations of 2 μl/cm$^3$ and 0.75 μ/cm$^3$ of a soil carrier/medium component provided good control of *Rhizoctonia* and *Pythium* damping-off, respectively, of sugar beet. A concentration of 5 μl/cm$^3$ sand provided 100% mortality in 24 h for *M. incognita*. By comparison, using in vitro studies, this same rate of the biorational provided fewer root knot galls than an *M. albus* infested ground barley formulation applied at 5 g/l of sand.

Example 15

Figure 5:
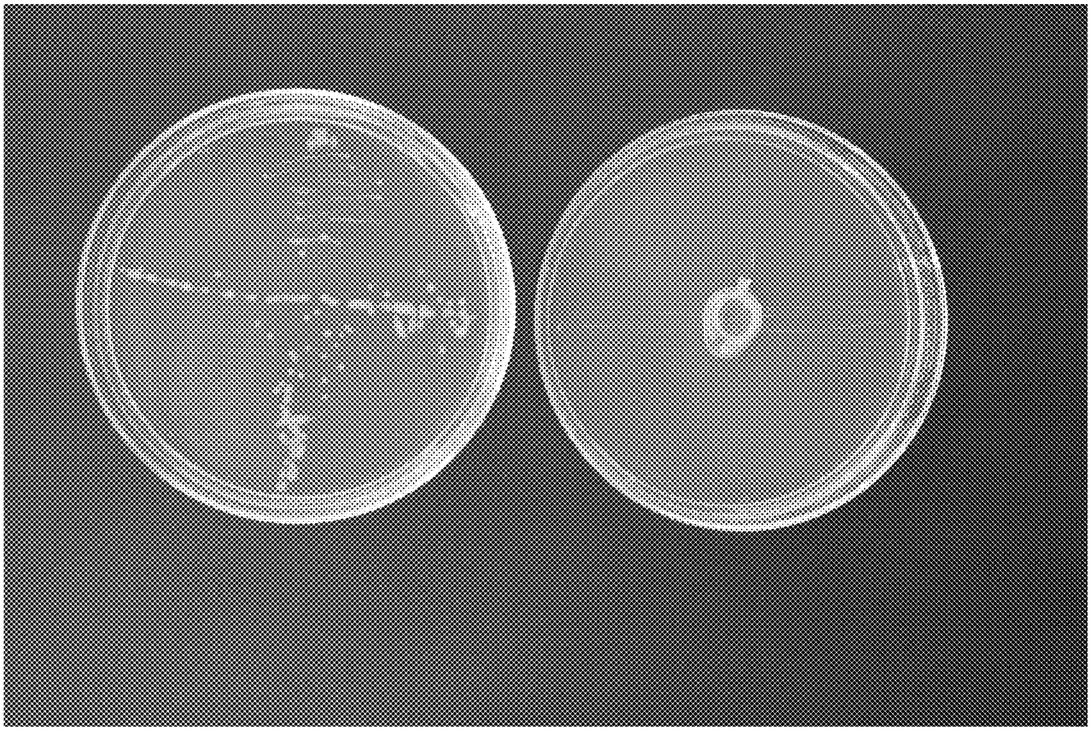
FIG. 5. Demonstrating effect against tomato rot/wilt, on the left is the control plate of *C. michiganense*, and on the right is the plate treated with 20 microliters an FFC composition of this invention.

*Corynebacterium michiganese* causes serious tomato loss through tissue wilt and rot. An authentic culture of this bacterium was streaked on nutrient broth agar and a small cap was placed in the middle of the plate. Into the cap was placed 20 microliters of the an artificial, lab-prepared FFC composition of this invention. A control plate contained no FFC composition. The plates were incubated for 24 hr., then examined. There was no growth of the bacterium on the FFC-treated plate. (See, FIG. 5.) As such, an FFC composition of this invention can be used, without limitation, to treat tomato seeds, plants or produce. Alternatively, an FFC composition can be mixed with water as a pre-bed soil drench.

Example 16

With reference to the preceding and consistent with several of the foregoing examples, a range of FFC compostions of this invention can be used either prophylactically or in the treatment of active disease states, such disease including, without limitation, diseases affecting sugar beet, tomato, onion, grain, banana and plantain, and citrus crops among others.

More generally, the present compostions and methods can be directed to the treatment and enhanced viability of seeds, plants, produce and/or related food products—whether prophylactically or in the presence of fungal or bacterial microbes, regardless of lifecycle stage (e.g., zoospore, etc.), development, growth or extent of infection. Accordingly, as would be understood by those in the art, such compositions can comprise and/or be applied, irrespective of form (e.g. powder, granules, liquid, mist, suspension, vapor, pastes, gels, coatings, etc.), on the surface of or in contact with a seed, seedling or plant (e.g., roots, stems, leaves, etc.) or produce therefrom (e.g., either pre- or post-harvest).

Example 17

FFC compositions and/or components thereof, either alone or as can be incorporated into various other compositions, can be employed in a variety of end-use applications in the poultry, produce and related food-processing industries. Several such non-limiting applications are provided in the following examples.

Example 17a

An FFC composition of this invention, in accordance with compositions of the sort described in Tables 2-7 and 10, is used to treat a range of egg products, including but not limited to whole egg, and liquid whole egg, fortified whole egg, and liquid fortified whole egg, salt whole egg, and liquid salt whole egg, sugar whole egg, and liquid sugar whole egg, and blends of such products—whether or not liquid—with sugar, syrup solids, syrups, dextrose and dextrins and/or gums and thickening agents, together with scrambled egg mixes and liquid scrambled egg mixes, reduced cholesterol egg products and liquid products and blends thereof, and related products containing less than about 10% egg solids, shell eggs and egg components including but not limited to decholesterolized egg yolk. Such terms will be understood by those skilled in the art and have standard meanings in accordance with accepted industry and regulatory usage.

Example 17b

Likewise, various FFC compositions of this invention, including but not limited to those utilizing propanoic acid in at least partial substitution for isobutryic acid, can be used in the preparation and/or packaging of extended shelf life (ESL) liquid egg products, including but not limited to whole egg, scrambled mixes, egg yolk and egg white liquid products.

Example 17c

Likewise, various FFC compositions of this invention can be used in the processing of cracked, empty egg shells. As would be understood in the art, using available techniques and processing equipment, an FFC composition and/or a component thereof—alone or as incorporated as part of another composition—can be applied (e.g., sprayed on) to empty shells before further processing, for instance into a nutraceutical product. Likewise, one or more compositions of this invention can be applied to or incorporated with or otherwise used to treat poultry carcass, meat or a related meat product, using apparatus and techniques known in the art. By extension, one skilled in the art would understand that the present invention can also be utilized with other types of animal carcass, meat, processed meat products and all other forms of animal flesh (e.g., mammals, birds, fishes, snails, clams, crustaceans, seafood and other edible species), as also illustrated in one or more of the following examples.

Example 17d

As an extension of the preceding example, such an FFC composition can be incorporated into such a processed nutraceutical product (e.g., herbal and spice capsules or tablets) to inhibit bacterial/fungal growth.

Example 17e

While the preceding examples illustrate various downstream processing applications, the present invention can be utilized more widely in the context of egg and poultry production. Without limitation, FFC compositions or related components of this invention can be introduced to any poultry or egg production facility and/or applied to any equipment or machinery associated therewith. For instance, air or surface treatment of a coop or growing/laying facility can control, reduce and/or inhibit airborne and surface-deposited contaminants and subsequent microbial growth thereon.

Example 18

An FFC composition or one or more components thereof can be incorporated into a variety of other processed food products, including food products having a water activity otherwise supportive of microbial growth. For instance, such a composition or component can be incorporated into humus, peanut butter and other such spreads, dips and mixtures. Relating to the peanut growing and processing industries, compositions and related components of this invention can be applied to peanuts before and after the shells are cracked, after an initial peanut wash, to a related processed product (e.g., peanut butter) and/or on packaging equipment and packing materials.

Example 19

Likewise, an FFC composition/component of this invention (e.g., one or more of or compositions of Tables 2-7 and 10, above, or variations of the sort described therein) can be used as or incorporated into a variety of skin care or treatment products, regardless of formulation (e.g., lotion, ointment, cream, etc.).

Example 19a

For instance, acne is commonly caused by one or more bacterial species invading skin follicles. Demonstrating further use of this invention, an aqueous formulation of a propanoic acid-substituted FFC composition of this invention was prepared and used to treat an adolescent male subject presenting age-related acne. One application every three days for three weeks significantly reduced, by visual observation, the number and intensity of acne lesions.

Example 19b

Figure 6:
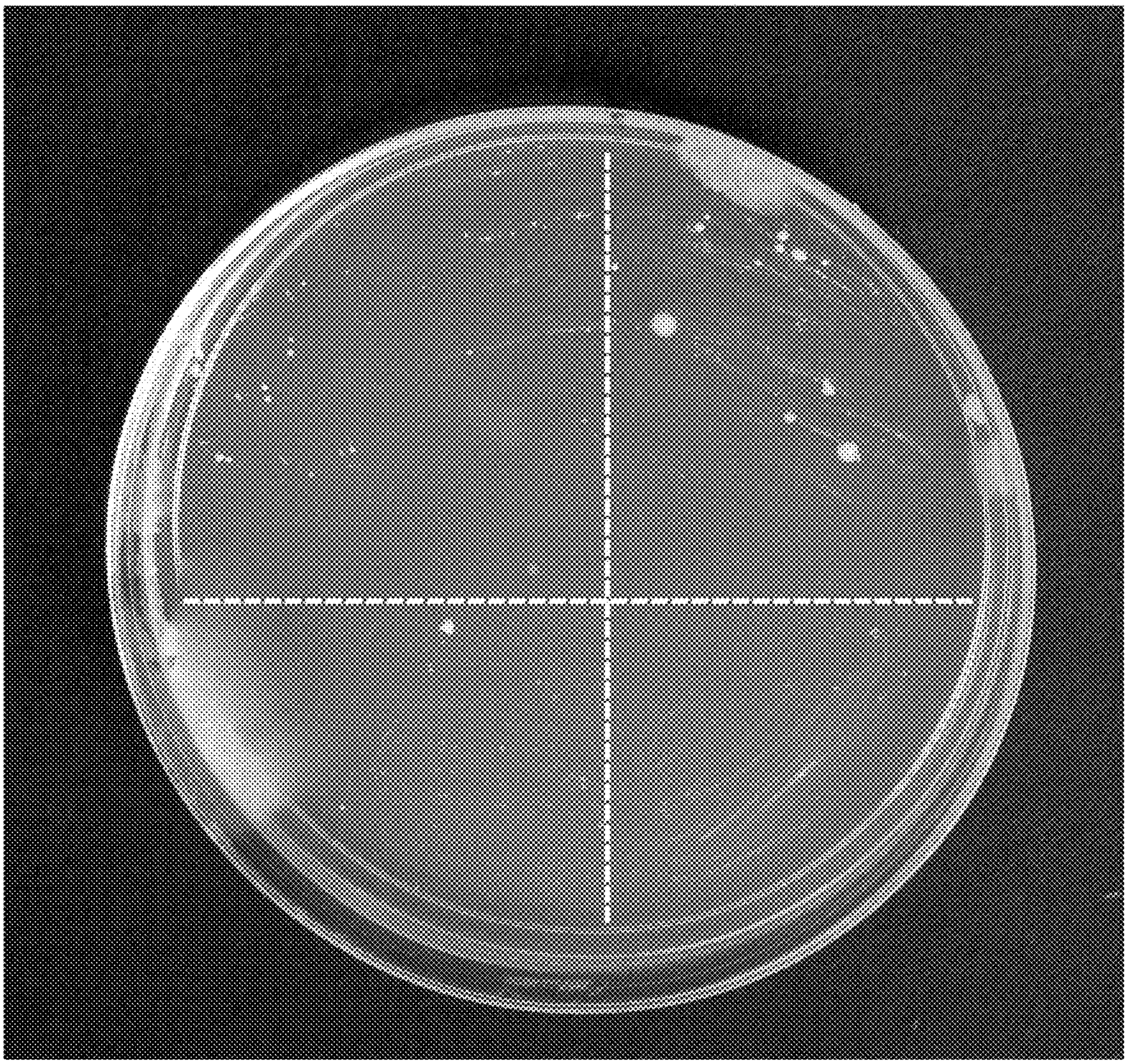
FIG. 6. Demonstrating effect of an FFC composition of this invention incorporated into a skin cream product.

Demonstrating another use of this invention in the context of a consumer and/or health care product, an FFC composition of this invention was incorporated (at approximately 2% by weight) in a representative over the counter skin cream preparation. With reference to FIG. 6, a PDA plate was prepared and incubated for one day with a control cream (without FFC component or composition), top left; a control cream contaminated with bacterial cells, top right; "treated" cream with FFC composition, bottom left; and treated cream with bacterial contamination, bottom right. As shown, bacterial growth in such a skin cream product was prevented by incorporating a modest concentration of an FFC composition of this invention.

Example 20

Likewise, this invention can be utilized in conjunction with a range of oral hygiene, care and treatment products. Without limitation, the following examples demonstrate such use of a propanoic acid-substituted FFC composition of the sort described above. Alternatively, various other FFC compositions can be used, in accordance with compositions of Tables 2-7 and 10, above, or variations thereof as described elsewhere herein.

Example 20a

For instance, illustrating one such oral care/hygiene product, a mouthwash/rinse product was formulated utilizing about 1% of such an FFC composition. Such a product was prepared by incorporation of such an FFC composition into a commercially-available, off-the-shelf mouthwash/rinse product. FFC compositions of this invention, regardless of concentration or dose level, can also be incorporated into a tooth paste/gel or related gum, mouth, oral or dental care product.

Example 20b

Lichen planus (LP) is an autoimmune disease of the skin that can occur inside the mouth or on other mucous membranes. As membranes become unstable, bacteria or fungi can take up residence in these areas and cause pain, reddening, infection, bleeding and swelling of the tissues. In order to reduce the cause of extraneous involvement of bacteria in this disease, a mouth wash product was prepared containing a 1% aqueous solution of such an FFC composition. The mouth of the patient was rinsed twice to three times daily for at least 3-4 minutes and then spit out. Photos were taken before the treatments were applied and after three weeks of treatment. After 3 weeks, the results showed an almost total reduction of gum reddening, accompanied by a nearly totally reduction of mouth and gum pain as well as a return to near normal color of the gums and other mucous membrane color. The patient reported a near-total cessation of pain/bleeding and the most relief from LP, as compared to prior experience.

Example 20c

A 1% solution of the aforementioned FFC composition in an off-the-shelf mouth rinse was used to reduce dental plaque and treat other problems arising from bacteria associated with oral problems. Daily use, with 3-4 mouth rinses/day, for two months resulted in little or no dental plaque build-up. Gums that were initially recorded as red, swollen, and easily caused to bleed (from notes actually taken by the dentist) now appeared as normal in color and did not bleed upon probing with the "explorer" instrument.

Example 20d

To confirm effectiveness of such an FFC composition, mouth spittle resulting from the previous example was placed on one side of a nutrient agar plate, spittle from a non-FFC commercial mouth rinse was placed on the other side of the same plate, and non-rinse spittle was placed on another plate. The spittles were then incubated for two days. By comparison: the non-rinse spittle had a high bacterial load; the non-FFC rinse spittle had, as expected, a reduced bacterial load; but the FFC-rinse spittle had no detectable bacteria.

Example 20e

In another example, an oral surgeon tested an FFC composition (e.g., as 1% of a commercial rinse/wash product) prior to oral surgery. The patient placed non-treated spittle on an agar plate (nutrient agar), rinsed with the FFC-rinse solution and placed that spittle on another agar plate. After two-three days of incubation there were no bacterial colonies on the FCC-rinse treated plate, indicating use before and after oral surgery to treat or inhibit tooth or other oral infections.

Example 21

Mastitis in milk cows is caused by a complex of bacteria associated with the utter. In accordance with various non-limiting embodiments of this invention an FFC composition or a rhamnolipid modified FFC composition of the sort described below can be applied to the utter at the time of milking to reduce the prospect of bacterial infections and contamination of milk product.

Example 22

Various FFC compositions of this invention can be used to reduce microbial loads on industrial/medically important biofilms. With regard to the latter, items ranging from dental prostheses to artificial joints, can be treated with an FFC composition of this invention before surgical implantation.

Example 23

FFC compositions of this invention can be used to control fungal and bacterial decay of clothing items especially those exposed to moist environments (i.e. leathers, shoes, boots, straps, ties, belts). For instance, application of 0.2 ml of a 1% FFC composition of the sort described above was placed in boots that had become totally wet. The boots were enclosed to maintain the resulting vapors for a few hours, then exposed to dry air. The results showed no decay, and the boots dried without a residual moldy smell.

Example 24

Compositions of the present invention can comprise various FFC components and can be formulated as would be understood by those skilled in art made aware of this invention. Without limitation, regardless of end-use application or treatment, one or more of the present FFC components and/or related compositions can be incorporated into various antibacterial or antimycotic compositions. Without limitation, such a composition can comprise a rhamnolipid surfactant component—either alone or in conjunction with an antibacterial and/or antimycotic component of the sort known in the art. With respect to the latter, such compostions can comprise a syringomycin and/or a pseudomycin component.

Figure 7A:
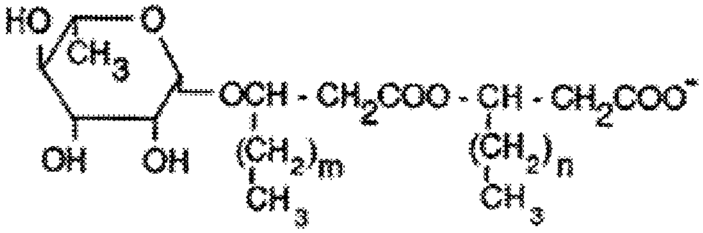
FIGS. 7A-B and 8 illustrate structures of several non-limiting, representative monorhamnolipid and dirhamnolipid compounds, in accordance with certain non-limiting embodiments of this invention.
Figure 7B:
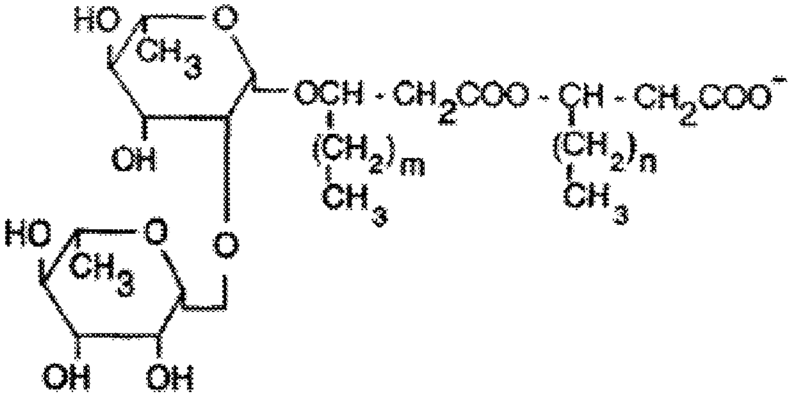
Figure 8:
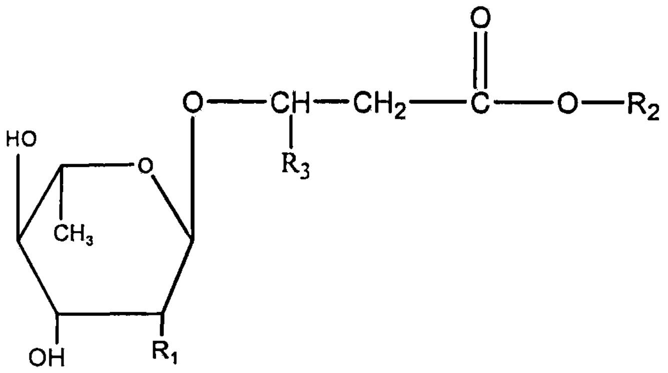

More specifically, as would be understood by those skilled in the art, a rhamnolipid component can comprise one or more compounds of the sort described in U.S. Pat. Nos. 5,455,232 and 5,767,090, each of which is incorporated herein by reference in its entirety. Such a rhamnolipid compound, whether presently known in the art or hereafter isolated and/or characterized, can be of a structure disclosed therein or varied, as would also be understood by those skilled in the art. For example, without limitation, whether synthetically-derived or naturally occurring (e.g., from a *Pseudomonas* species or a strain thereof) in an acid form and/or as a corresponding acid salt, such a compound can be alkyl- and/or acyl-substituted (e.g., methyl and/or acetyl, respectively, and higher homologs thereof) at one or more of the saccharide hydroxy positions. Likewise, whether in mono- and/or dirhamno form, any such compound can be varied by hydrophobic moiety. As a non-limiting example, with reference to FIGS. 7A and 7B, m and n can independently range from about 4 to about 20, regardless of whether such moieties are saturated, monounsaturated or polyunsaturated, whether the hydrophobic moiety is protonated, present as the conjugate base with any counter ion or otherwise derivatized. Consistent with broader aspects of this invention, a rhamnolipid useful in such compositions is structurally limited only by resulting surface active function and/or antimicrobial effect in conjunction with an FFC composition of this invention. Accordingly, structural variations of the sort described in International Publication WO 99/43334 are also considered in the context of this invention, such publication incorporated herein by reference in its entirety. See, also the non-limiting rhamnolipid components/structures of FIGS. 8-9.

Without regard to antimicrobial or rhamnolipid identity, a carrier component of the inventive compositions can comprise a fluid selected from, but not limited to, water, an alcohol, an oil, a gas and combinations thereof. For instance, while such compositions are unlimited with respect to amount or concentration (e.g., wt. %) of antimicrobial or rhamnolipid quantities, a carrier comprising water and/or an alcohol can be used to facilitate desired formulation, shipping, storage and/or application properties, as well as effective concentration and resulting activity.

Such rhamnolipid surfactant components, antimycotic components and/or related compositions include but are not limited to those described in co-pending application Ser. No. 11/351,572, in particular examples 9-15 thereof, such application filed on Feb. 10, 2006 and incorporated herein by reference in its entirety. Such rhamnolipid surfactant components, antimycotic components and/or related compositions can incorporate or be used in conjunction with one or more FFC components and/or FFC compostions of the present invention. Such antibacterial and/or antimycotic components are known to those skilled in the art and commercially available. Various rhamnolipid components and related surfactant compositions are available from Jeneil Biosurfactant, LLC, under the Zonix trademark.

Example 25

For instance, illustrating such rhamnolipid-related variations, a range of compositions can be prepared with one or more rhamnolipid components and one or more FFC compositions of this invention (and/or one or more FFC components thereof), for use as or in conjunction with a post-harvest wash or treatment of a wide range of fruits and vegetables. Without limitation, in such a composition, a rhamnolipid component, (e.g., as described in the aforementioned '572 application) can be present in an amount ranging from about 0.1 wt. % to about 99.9 wt. %, and an FFC composition/component (e.g., compositions of Tables 2-7 and 10, above) can be present in an amount ranging from about 99.9 wt. % to about 0.1 wt. %. With reference to applicable EPA regulations, there is no tolerance limit for the aforementioned Zonix rhamnolipid surfactants. Likewise, there is no tolerance limit for the FFC compositions/components of this invention. Accordingly, food treated with such rhamnolipid/FFC compositions can be consumed without further washing.

Example 25a

In accordance with the foregoing, a rhamnolipid/FFC composition can be used to wash citrus fruits. One such wash/bath composition was prepared using an 8.5% rhamnolipid solution (in water) and a 5% FFC solution (e.g., the composition of Table 10 in water). One gallon of a 95:5 (v/v) mixture was diluted to 425 gallons. Using procedural protocols known in the industry or otherwise required under applicable state or federal regulations, the composition was used effectively to clean and penetrate citrus peel—killing both surface and interior bacteria and fungi. While effective results were demonstrated with citrus fruit, this and related rhamnolipid/FFC compositions can be used comparably in conjunction with post-harvest wash or treatment of any fruit or vegetable (e.g., without limitation, blueberries, tomatoes, grapes, onions, sugar beets, sweet potatoes, apples, pears, pineapples and various other tropical produce such as but not limited to noni and acai fruit, etc.). Fruits/vegetables washed or treated with FFC compositions of this example would be recognized as safe and hygienic for human consumption.

Example 25b

Whether or not having an incorporated rhamnolipid component, various FFC compositions of this invention can be used to treat various fruits and vegetables (e.g., without limitation, pears, peaches, apples, tomatoes, apricots, mangos and the like) before or upon packaging or canning to reduce bacterial/fungal loads.

Example 26

Sourcing of FFC Component Compounds. Component compounds for use in compositions of this invention can be obtained commercially or prepared using synthetic techniques of the sort well-known or otherwise described in the literature. (See, e.g., U.S. Pat. No. 6,911,338, the entirety of which is incorporated herein by reference.)

Alternatively, as can be preferred in conjunction with certain embodiments—including but not limited to animal and human food and beverage items, personal care and cosmetic products and related processing and manufacturing techniques, GRAS component compounds and related FFC compositions of this invention can be derived naturally through fermentation techniques, and are available under the Flavorzon trademark from Jeneil Biotech, Inc. of Saukville, Wisconsin. Accordingly, various compositions of this invention, depending on end-use or application, can comprise compounds derived from bacterial fermentation, compounds chemically synthesized and various mixtures of compounds of fermentative and synthetic origin.

With reference to the preceding, the following examples illustrate non-limiting use or incorporation of one or more compositions of this invention, such use or incorporation as would be understood by those skilled in the art made aware of this invention, and described in the context of several prior patents, each of which is incorporated herein by reference for purpose of demonstrating that one skilled in the art would understand such use or incorporation of this invention.

Example 27

Illustrating other embodiments, various compositions of this invention can be formulated for use as an additive for a fruit drink, such as described in the incorporated U.S. Pat. No. 6,566,349. For instance, compositions of this invention may be added to a juice in combination with or as a substitute for a flavonoid compound and/or an antioxidant, or may be pre-applied to fruits and vegetables before processing, to increase product shelf life. As would be understood by those skilled in the art, such compositions of the '349 Patent can be modified to include one or more compositions of the present invention in an amount of which for any end-use application can be determined, in a straightforward manner without undue experimentation.

Example 28

Compositions of the present invention can also be formulated for use in preserving tea and tea/fruit mixture beverages, such as described in the incorporated U.S. Pat. No. 5,866,182. For instance, compositions of the present invention may be used in combination with or as a replacement for K-sorbate and/Na-benzoate, ascorbic acid, and dimethyl dicarbonate. As will be understood by those skilled in the art, such beverages of the '182 Patent (e.g., example 1 thereof) may be modified to include one or more compositions of the present invention, an amount of which for any particular application may be determined in a straight-forward manner without undue experimentation.

Example 29

Compositions of the present invention can also be formulated for use in preserving and/or enhancing the antimicrobial effect of antiperspirants and deodorants, such as described in the incorporated U.S. Pat. No. 5,176,903. For instance, compositions of the present invention can be used in combination with or as a replacement for parabens, imidazolidinyl urea, quaternium-15, benzyl alcohol, phenoxyethanol, and various other suitable preservatives (e.g., as described in examples 1-3 thereof) and added to such antiperspirant/deodorant to protect against degradation, extend shelf life and/or enhance effectiveness, one or more such compositions in an amount of which can be determined in a straight-forward manner without undue experimentation by one having ordinary skill in the art.

Example 30

Compositions of the present invention can also be formulated for use in antiperspirants, such as described in the incorporated U.S. Pat. No. 4,548,808. For instance, one or more compositions of the present invention can be added to the substantially anhydrous non-alcoholic antiperspirant products described in the '808 Patent (e.g., examples 1-6 thereof) in effective amounts readily determined without undue experimentation by one having ordinary skill in the art—to extend shelf-life and enhance antimicrobial effect.

Example 31

Compositions of the present invention can also be formulated for use in animal/pet food, for example dog food, such as described in the incorporated U.S. Pat. No. 3,119, 691. One having ordinary skill in the art would recognize that one or more of the present compositions can be added to low hydration dog food, high moisture dog food, and rehydratable dog food to (e.g., to the product formulations described therein) prolong the shelf-life of products disclosed in the '691 Patent, such composition(s) in an amount readily determined without undue experimentation.

Example 32

Compositions of the present invention can also be formulated for use in cat litter, such as described in the incorporated U.S. Pat. Nos. 5,060,598 and 4,721,059. Various absorbent materials, including, for example, clay, alfalfa, wood chips, and saw dust, and increased absorbent materials including clay-like filler ('059 Patent) and peat ('598 Patent) are used to absorb urine and control odor. One or more compositions of the present invention may be used in conjunction with these materials (e.g., sprayed on or otherwise incorporated into) to reduce or eliminate microbial activity and control odor after use of the litters, such composition(s) in an amount readily determined without undue experimentation.

Example 33

Compositions of the present invention can also be formulated for use in spray disinfectant applications, such as described in the incorporated U.S. Pat. No. 6,250,511. The '511 Patent describes including a treatment solution in the spray bottle comprising between about 25% and 75% of at least one glycol compound, between 0.2% and 60% of an antimicrobial component, between about 5% and 45% of a surfactant, and optionally effective amounts of fragrances, dyes and other additives (at col. 3 thereof). For instance, one or more compositions of the present invention can be used in conjunction with a disinfectant of the '511 Patent as a replacement for the antimicrobial component, or as an additive thereto, such composition(s) in an amount readily determined by one skilled in the art without undue experimentation.

Example 34

Compositions of the present invention can also be formulated for cleaning and/or disinfecting food and beverage processing equipment, such as described in the incorporated U.S. Pat. No. RE 40,050. While the '050 Reissue teaches a halogen dioxide composition, such a formulation could be modified by one skilled in the art to substitute one or more compositions of the present invention, such composition(s) in an amount readily determined without undue experimentation and contacted with or applied to such processing equipment using apparatus and techniques of the sort described in the '050 Reissue (e.g., as described in cols. 3-4 thereof).

Example 35

Compositions of the present invention can also be formulated for use in preserving wood, such as described in the incorporated U.S. Pat. No. 4,988,576 (and for lignocellulosic-based composites described in incorporated U.S. Pat. No. 7,449,130). The '576 Patent teaches impregnating wood with a solution of a preservative composition comprising a graft copolymer of lignosulfonate, hydroxyl benzyl alcohol and a metal salt or a mixture of metal salts, or alternately of at least one metal salt of a graft copolymer of lignosulfonate, the copolymer being a reaction product of lignosulfonate and acrylic monomers. For instance, one or more compositions of the present invention may be used alone or in combination with such preservatives taught by the '576 Patent (or the '130 Patent), as described, respectively, in examples 1-4 and 1-2 thereof, to impregnate and preserve wood, such composition(s) in an amount readily determined by one having ordinary skill in the art without undue experimentation.

Example 36

Compositions of the present invention can also be formulated for use with sanitizing and/or disinfecting wipes, such as described in the incorporated U.S. Pat. No. 4,575, 891, which teaches a pad partially saturated with a disinfectant (e.g., col. 2 thereof). The '891 Patent describes suitable disinfectants as alcoholic solutions, and other antiseptic solutions. For instance, one or more compositions of the present invention may be used alone or in combination with such disinfectants and incorporated into such a wipe material, such composition(s) in an amount readily determined and incorporated by one skilled in the art without undue experimentation.

Example 37

Compositions of the present invention can also be formulated for use with a hand sanitizing lotion, such as described in the incorporated U.S. Pat. No. 6,187,327. For instance, one or more compositions of the present invention can be formulated to be added to and work in conjunction with the lotion of the '327 Patent or to replace any of the active ingredients of the lotion to improve antimicrobial effect. The '327 Patent also discloses various other known hand sanitizers (e.g. an amphoteric-cationic surfactant, a cationic surfactant, a wetting agent, and a nonionic regressing agent). Regardless, a composition of the present invention can be incorporated as a replacement for or use in conjunction with any of the active ingredients in any such hand sanitizer, such composition(s) in an amount readily determined without undue experimentation.

Example 38

Compositions of the present invention can also be formulated for use in treating edible or crop seeds, such as described in the incorporated U.S. Pat. No. 4,581,238, which teaches contacting with seeds with steam having a sorbate dispersed therein (e.g., in cols. 2-5 thereof). For instance, using techniques and apparatus disclosed therein, one or more compositions of the present invention can be volatilized or otherwise applied to such seeds, such composition(s) in an amount readily determined by one having ordinary skill in the art without undue experimentation.

Example 39

Compositions of the present invention can also be formulated for use in preventing or inhibiting the growth of spoilage organisms, such as described in the incorporated U.S. Pat. No. 4,356,204, which teaches contacting food with an effective growth inhibiting amount of a ketohexanoic acid (e.g., in cols. 2-3 thereof). One or more compositions of the present invention can be used alone or with such a ketohexanoic acid to further inhibit and/or kill spoilage organisms. Likewise, incorporated U.S. Pat. No. 2,711,976 suggests the use of amino acids to increase the resistance of custard foods to spoilage organisms and *Staphylococcus* species. Again, one or more compositions of the present invention may be used alone or in combination with or as a substitute for such amino acids. Likewise, incorporated U.S. Pat. No. 2,866,819 suggests the use of sorbic acid as a preservative in foods. Again, one or more compositions of the present invention may be used alone or in combination or as a substitute for sorbic acid. Likewise, incorporated U.S. Pat. No. 2,910,368 discloses the use of EDTA with sorbic acid to increase the shelf life of vegetables. Again, one or more compositions of the present invention may be used alone or in combination with EDTA and/or sorbic acid. In each instance, such composition(s) of the present invention can be used in an amount readily determined by one skilled in the art without undue experimentation.

Example 40

Compositions of the present invention can also be formulated for use in treating fruit, seeds, grains, and legumes, such as described in the incorporated U.S. Pat. No. 5,273,769, which teaches placing any of the items to be treated in a container then introducing carbon dioxide and ammonia. For instance, using apparatus and techniques described therein (e.g., examples 1-4), one or more compositions of the present invention may be utilized effectively as would be understood in the art without undue experimentation.

Example 41

Compositions of the present invention may also be formulated for use in treating dental and medical articles/devices and implants, the latter as more specifically described in the incorporated U.S. Pat. No. 6,812,217, which teaches an antimicrobial polymer film applied to the exterior surface of an implantable medical device. For instance, using techniques of the sort described therein, one ore more compositions of the present invention may also be deposited on or otherwise incorporated with such a device or article (whether medical or dental) or polymer film thereon (e.g., as described in cols. 5-6) to provide antimicrobial effect, such composition(s) in an amount readily determined by one of ordinary skill in the art without undue experimentation.

Example 42

Compositions of the present invention may also be formulated for use in treatment of textiles, such as in the incorporated U.S. Pat. No. 5,968,207, which teaches application of triclosan ester to textile fibers or fabric by diffusion or impregnation. For instance, one or more compositions of the present invention may be formulated for use alone or in combination with such compound to improve anti-microbial properties of a textile or fibers thereof, whether a man-made, natural, or a blend (e.g., as described in cols. 2-3 of the '207 Patent), such composition(s) in an amount readily determined by one of ordinary skill in the art without undue experimentation.

Example 43

Compositions of the present invention can be formulated for treatment of surfaces of a food processing facility, related equipment and foodstuffs, such as described in the incorporated U.S. Pat. No. 7,575,744. For instance, using techniques and apparatus of the sort described therein, one or more compositions of the present invention may be formulated and disposed on equipment and foodstuff surfaces in a wide range of food processing facilities to reduce or eliminate microbial activity, such facilities/equipment including but not limited to snack, poultry, citrus, peanut and related food processing facilities/equipment (see, e.g., col. 20). Such composition(s) can be employed in an amount readily determined by one skilled in the art without undue experimentation.

Example 44

Compositions of the present invention can also be formulated for use in the treatment of microbial-related diseases (i.e., mastitis, hoof & mouth, etc.) in farm animals and livestock, and to inhibit microbial growth on crops, plants, grains, and other foodstuffs, such as described in the incorporated U.S. Pat. No. 7,192,575, which teaches application of and a composition comprising clove bud oil, eucalyptus oil, lavender oil, tea tree and orange oil. For instance, one or more compositions of the present invention can be formulated for use alone or in combination with that of the '575 Patent (e.g., examples 1-2 thereof), such composition(s) in an amount readily determined by one of ordinary skill in the art without undue experimentation.

Example 45

Compositions of the present invention can also be formulated for use in preserving foodstuffs such as dressings, sauces, marinades, condiments, spreads, butters, margarine, dairy based foods, and the like from microbial spoilage, such as described in the incorporated U.S. Pat. No. 6,156,362, which teaches a combination of antimicrobial components. One or more compositions of the present invention can be formulated for use alone or in combination with one or more of the components of the '362 Patent (e.g., examples 1-4 thereof), such composition(s) or in an amount readily determined by one of ordinary skill in the art without undue experimentation.

Example 46

Compositions of the present invention can be formulated for incorporation with a wide range of water-based and organic-based paints, stains and related surface coatings, such as described in the incorporated U.S. Pat. No. 7,659,326 and the authorities recited therein (e.g., Kirk-Othmer-Paint; pp. 1046-1049, Vol. 17; 1996, by Arthur A. Leman, the disclosure of which is also incorporated herein by reference in its entirety). For instance, one or more compositions of the present invention may be formulated for use or alone in combination with another antimicrobial component described in the detailed description and examples 1 and 3 of the '326 Patent, such composition(s) in an amount readily determined by one skilled in the art without undue experimentation.

Example 47

Compositions of the present invention can also be formulated for use or incorporation into after-shave products, such as those described in the incorporated U.S. Pat. No. 6,231,845. For instance, one or more compositions of the present invention can be used in conjunction with components of the sort described in examples 1-6 of the '845 Patent, to provide antimicrobial effect to such after-shave products of the prior art. Such compositions can be present in an amount readily determined by one skilled in the art without undue experimentation.

Example 48

Compositions of the present invention can also be formulated for use or incorporation into a product for treatment of a carcass, meat or meat product (e.g., of mammals, birds, fishes, clams, crustaceans and/or other forms of seafood, and other edible species), such as described in the incorporated U.S. Pat. No. 7,507,429. For instance, one or more compositions of the present invention may be formulated for use alone or in combination with another antimicrobial component, for incorporation into a product of the sort described in the '429 patent. Such composition(s) can be present in an amount readily determined by one skilled in the art without undue experimentation, and the corresponding product(s) can be applied or otherwise utilized with techniques and apparatus described in the '429 patent or as would otherwise be understood by those skilled in the art made aware of this invention. (See, e.g., the meat processing, spraying, immersing and treating, and composition and component sections of the detailed description of the '429 Patent.)

Example 49

Compositions of the present invention can also be formulated for use or incorporation into a material (e.g., a material for a coating or other incorporation) for a food product, such products including but not limited to snack foods, cereal foods and other food components, such snack and cereal foods and materials of the sort described in the incorporated U.S. Pat. No. 7,163,708. Without limitation as to how such materials can be applied, one or more compositions of the present invention can be used alone or in conjunction with one or more of the antimicrobial or preservative components of such materials, as described in the detailed description of food products and coating materials, of the '708 patent. Accordingly, as would be understood by one skilled in the art, such a composition can be present in an amount readily determined without undue experimentation.

Example 50

Compositions of the present invention can be formulated for incorporation with a variety of edible spread compositions, including but not limited to peanut butter compositions, such as those described in the incorporated U.S. Pat. No. 7,498,050. For instance, as would be understood by one skilled in the art, one or more compositions of the present invention can be used in conjunction with such edible spread products to provide or otherwise enhance antimicrobial effect, as described in examples 1-2 of the '050 Patent, such composition(s) as can be present in an amount readily determined without undue experimentation.

Example 51

Compositions of the present invention can be formulated for incorporation with a wide range of pest control compositions, such as those described in the incorporated U.S. Pat. No. 6,720,450 (e.g., in sections 2-3 of the detailed description thereof). For instance, one or more compositions of the present invention may be formulated for use alone or in combination with another antipesticidal component, such as that described in the '450 patent. Likewise, one or more compositions of this invention can be formulated as described therein, with a suitable carrier component, for use against various blood-imbibing insects, including but not limited to various types of mosquitoes, and insect pests of agricultural crops. The present compositions can be used as described therein for direct contact, inhibition and/or elimination of mosquitoes, including the larvae, pupa and/or adult forms thereof. Alternatively, the present compositions can be used and/or formulated for repellent action. Regardless, such composition(s) can be present in an amount readily determined by one skilled in the art without undue experimentation and can optionally include a surfactant component. Such a surfactant can be a biosurfactant. Without limitation, such a biosurfactant can be selected from monorhamnolipids, dirhamnolipids and combinations thereof.

With reference to volatile by-products of *Muscodor* species and alternate compositions of the sort described in and available through use of the FFCs of Tables 2-7 and 10, the following examples demonstrate the use of several such FFC compositions and related articles, in accordance with this invention.

Example 52

Several assays were undertaken using representative antimicrobial compositions against various test organisms. Plugs of inoculum (3×3 mm) were streaked at a minimal level, then exposed, respectively, to vapors from compositions B-L placed in a microcup center well. Radial growth from each plug was measured (mm) after 38 hours at room temperature.

TABLE 14

| Test column | *Pythium* | Rhizoc | Vert | Asp | Phyto | Fus | Botr | Scl | *Bacillus* | *E. coli* |
|---|---|---|---|---|---|---|---|---|---|---|
| A | 31 | 8 | 2.5 | 3.5 | 3.0 | 9.5 | 5.5 | 7 | growth | growth |
| B | 0 | 0 | 0 | 1 | 0 | 0.2 | 0.5 | 1.7 | slight | 0 |
| C | 0 | 0 | 0 | 0.5 | 0 | 0.7 | 0.2 | 0.8 | trace | 0 |
| D | 0 | 0 | 0 | 0.45 | 0 | 0.7 | 0 | 0 | 0 | 0 |
| E | 0 | 0 | 0 | 0.4 | 0 | 0.5 | 0.1 | 0.7 | 0 | 0 |
| F | 0 | 0 | 0 | 0.1 | 0.1 | 0 | 0.1 | 0.7 | trace | 0 |
| G | 0 | 0 | 0 | 0.2 | 0.1 | 0.1 | 0.1 | 3.5 | 0 | 0 |
| H | 0 | 0 | 0 | 0.1 | 0.15 | 2.5 | 0.2 | 0.15 | 0 | 0 |
| I | 0 | 0 | 0 | 0.15 | 0 | 0.3 | 0.1 | 0.15 | 0 | 0 |
| J | 0 | 0 | 0 | 0.7 | 0 | 0.1 | 0 | 0 | 0 | 0 |
| K | 0 | 0 | 0 | 0.7 | 0 | 0.3 | 0.15 | 1.7 | 0 | 0 |
| L | 0 | 0 | 0 | 0.07 | 0 | 1.5 | 0 | 0.8 | 0 | 0 |

Antimicrobial compositions tested:
A = control (no treatment)
B = a composition of Table 10, above; 10 microliters
C = propanoic acid:isoamyl acetate, 7:2 (v/v); 9 microliters
D = propanoic acid:isobutyl isobutyrate, 7:2 (v/v); 9 microliters
E = propanoic acid:isopentyl isobutyrate, 7:2 (v/v); 9 microliters
F = propanoic acid:allyl acetate, 7:2 (v/v); 9 microliters
G = propanoic acid:methyl isobutyrate, 7:2 (v/v); 9 microliters
H = propanoic acid:phenylethyl acetate, 7:2 (v/v); 9 microliters
I = propanoic acid:benzaldehyde, 7:2 (v/v); 9 microliters
J = propanoic acid:isoamyl acetate:benzaldehyde, 7:2:2 (v/v/v); 11 microliters
K = propanoic acid:all esters above in equal mix, 7:2 (v/v); 9 microliters
L = propanoic acid:all esters above in equal mix:benzaldehyde, 7:2:2 (v/v/v); 11 microliters.

Test Organisms: *Pythium ultimum* (*Pythium*); *Rhizoctonia solani* (*Rhizoc*); *Verticullum dahliae* (Vert); *Aspergillus fumigatus* (Asp); *Phytophthora cinnamomi* (*Phyto*); *Fusarium solani* (Fus); *Botrytis cinerea* (Botr); *Sclerotinia sclerotiorum* (Scl); *Bacillus subtilus* (*Bacillus*); and *Escherichia coli* (*E. coli*).

As demonstrated above, specific compositions of this invention can be designed for differential antimicrobial effect. For instance, while composition B was somewhat less than advantageous against the *Botrytis* and *Sclerotinia* species, composition D inhibited growth completely, under the assay conditions employed. Regardless, an antimicrobial composition of this invention—whether used neat, in vapor form or incorporated with a carrier component—can show beneficial results with a propanoic acid component present at a ratio of at least about 7:about 1 with respect to any other composition component. (See FIG. 10 for structures and nomenclature of FFCs employed in compositions B-L.)

Example 53

Figure 11B:
FIGS. 11A-B provide digital images of (A) post-harvest produce preserved over 7 days in the presence of bentonite granules impregnated with an antimicrobial composition of this invention; and, by comparison, (B) a control system showing spoilage after 7 days in the presence of granules without an incorporated antimicrobial composition.
Figure 11A:
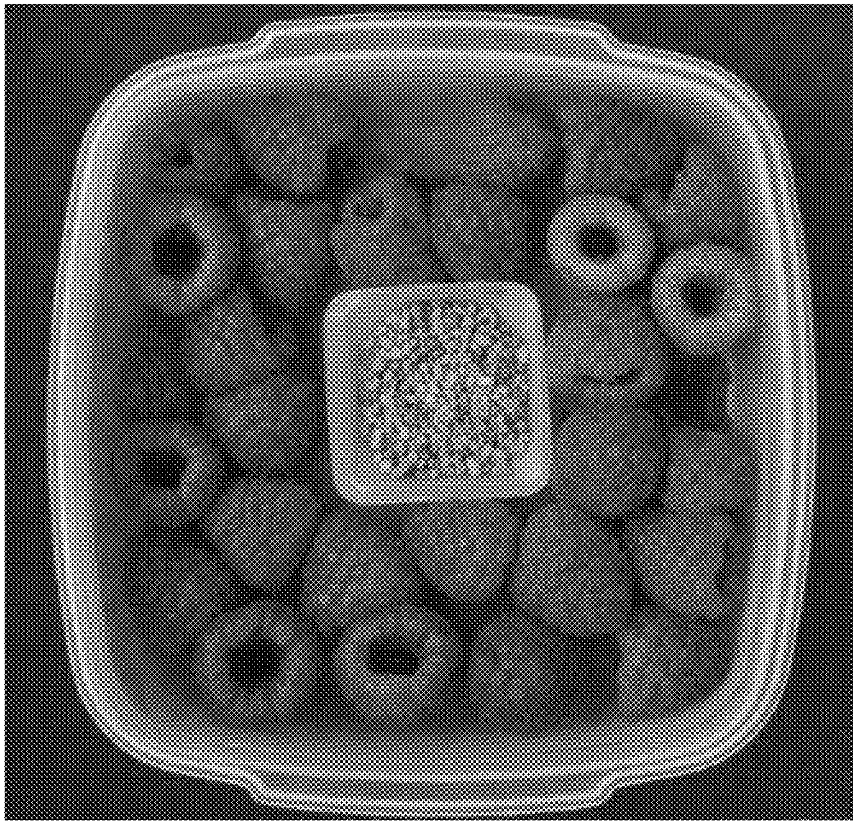

In accordance with and illustrating use of various articles of this invention, granules of bentonite clay (e.g., from A1 Harvey of Lovell, Wyoming) were impregnated with a representative composition of Table 10, above, (~0.80 ml/g of bentonite) and placed in an open-top enclosure. Granules of this article and part of a bunch of raspberries (i.e., a post-harvest perishable food item) were placed in a sealed container. After seven days, little mold or other microbial growth was evident. (See, FIG. 11A.) By comparison, using a control system of bentonite granules without incorporated antimicrobial composition, raspberries from the same bunch were stored in a sealed container over the same time period: excessive spoilage was observed. (See, FIG. 11B.)

Example 54

Various other compositions of this invention, including without limitation compositions B-L of Example 52, can be incorporated with a solid carrier component. For instance, commercially-available bentonite clay granules can be impregnated with such a composition, for use in conjunction with a vapor-permeable enclosure, such as a sealed or re-sealable flexible bag or pouch. Whether a suitably-dimensioned mesh or of a porous non-woven Tyvek® or functionally-similar material, such a bag/pouch can provide an article with all components (i.e., an antimicrobial composition, a carrier and an enclosure) meeting FDA specifications relating to food processing and contact.

Example 55

With reference to biomimetic compositions of *M. Crispans* provided in Tables 2-7 and 10 and Example 11, above, bentonite clay granules can be impregnated with a composition of Table 10, then packaged into a vapor permeable pouch, or similar such enclosure, and positioned proximate to a deposit or collection of human waste or refuse. Without limitation, such an article can be placed in or adjacent to a container of human waste—optionally, as a preliminary measure en route to a final treatment and/or disposal.

Example 55a

An antimicrobial composition useful in conjunction with the end-use application of example 55 is represented, below.

| |
|---|
| Acetaldehyde |
| Ethyl Acetate |
| Propanoic acid, 2-methyl-, methyl ester |
| Ethanol |
| Acetic acid, 2-methylpropyl ester |
| Propanoic acid, 2-methyl-, 2-methylpropyl ester |
| 1-Propanol, 2-methyl- |
| 1-Butanol, 3-methyl-, acetate |
| Propanoic acid, 2-methyl-, 2-methylbutyl ester |
| Acetic acid, 2-phenylethyl ester |

Example 55b

Another antimicrobial composition useful in conjunction with the end-use application of example 55 is represented, below.

| |
|---|
| Acetaldehyde |
| Ethyl Acetate |
| Propanoic acid, 2-methyl-, methyl ester |
| Acetic acid, 2-methylpropyl ester |
| Propanoic acid, 2-methyl-, 2-methylpropyl ester |
| 1-Propanol, 2-methyl- |
| 1-Butanol, 3-methyl-, acetate |
| Propanoic acid, 2-methyl-, 2-methylbutyl ester |
| Acetic acid, 2-phenylethyl ester |

Example 55c

Further, another antimicrobial composition useful in conjunction with the end-use application of example 55 is represented, below.

| |
|---|
| Ethyl Acetate |
| Propanoic acid, 2-methyl-, methyl ester |
| Acetic acid, 2-methylpropyl ester |
| Propanoic acid, 2-methyl-, 2-methylpropyl ester |
| 1-Propanol, 2-methyl- |
| 1-Butanol, 3-methyl-, acetate |
| Propanoic acid, 2-methyl-, 2-methylbutyl ester |
| Acetic acid, 2-phenylethyl ester |

Example 56

With further reference to Tables 2-7 and 10 and Examples 32-33, various FFC compositions of this invention can be used to prepare cat litter. For instance, bentonite clay granules are contacted or impregnated with an antimicrobial composition (e.g., 0.20 wt. % to about 10.0 wt. % or, in certain embodiments, about 1.0 wt. % to about 3.0 wt. %) of the sort represented below.

| wt. % | Compound |
|---|---|
| about 0.1-about 10 | Acetaldehyde |
| about 0.5-about 10 | Ethyl Acetate |
| about 0.1-about 10 | 2-Butanone |
| about 4-about 20 | Propanoic acid, 2-methyl-, methyl ester |
| about 1.5-about 15 | Ethanol |
| about 0.1-about 10 | Acetic acid, 2-methylpropyl ester |
| about 20-about 40 | Propanoic acid, 2-methyl-, 2-methylpropyl ester |
| about 0.1-about 10 | 1-Propanol, 2-methyl- |
| about 20-about 40 | 1-Butanol, 3-methyl-, acetate |

-continued

| wt. % | Compound |
|---|---|
| about 1.0-about 30 | Propanoic acid, 2-methyl-, 2-methylbutyl ester |
| about 2-about 10 | 1-Butanol, 3-methyl- |
| about 40-about 80 | Propanoic acid, 2-methyl- |
| about 0.1-about 10 | Acetic acid, 2-phenylethyl ester |

Alternatively, compositions of the sort described in Examples 52 (compositions B-L) and Examples 55a-55c can also be used in the preparation of such a litter article. Regardless, the relative amount of any such component can be adjusted for any particular formulation, desired antimicrobial effect and/or to accommodate the presence of any one or more additives of the sort described herein including but not limited to perfuming/fragrance agents.

What is claimed is:

1. A method, comprising:
providing a composition comprising:
propanoic acid;
an ester of a $C_2$-$C_5$ acid; and
a $C_2$-$C_8$ aldehyde;
wherein said composition is absent naphthalene and azulene derivative compounds;
wherein a ratio of propanoic acid to the ester of the $C_2$-$C_5$ acid to the $C_2$-$C_8$ aldehyde is 7:2:2; and
contacting at least one of a microbe and a substrate with said composition, said composition in an amount sufficient to inhibit microbial growth.

2. The method of claim 1 wherein the ester of a $C_2$-$C_5$ acid is selected from isoamyl acetate, isobutyl isobutyrate, and combinations thereof and wherein the $C_2$-$C_8$ aldehyde is benzaldehyde.

3. The method of claim 1 wherein said substrate is a food item.

4. The method of claim 3 wherein said food item comprises post-harvest produce.

5. The method of claim 4 wherein the ester of a $C_2$-$C_5$ acid is selected from isoamyl acetate, isobutyl isobutyrate, and combinations thereof and wherein the $C_2$-$C_8$ aldehyde is benzaldehyde.

6. The method of claim 1, wherein the ester of a $C_2$-$C_5$ acid is selected from isoamyl acetate, isobutyl isobutyrate, and combinations thereof and wherein the $C_2$-$C_8$ aldehyde is benzaldehyde.

7. The method claim 1, wherein the $C_2$-$C_8$ aldehyde is benzaldehyde.

8. A method, comprising:
providing a composition comprising:
propanoic acid;
an ester of a $C_2$-$C_5$ acid; and
a $C_2$-$C_8$ aldehyde;
wherein said composition is absent naphthalene and azulene derivative compounds; and
wherein a ratio of propanoic acid to the ester of the $C_2$-$C_5$ acid to the $C_2$-$C_8$ aldehyde is 7:2:2
contacting at least one of a microbe and a food item with said composition, said composition in an amount sufficient to inhibit microbial growth.

9. The method of claim 8 wherein the ester of a $C_2$-$C_5$ acid is selected from isoamyl acetate, isobutyl isobutyrate, and combinations thereof and wherein the $C_2$-$C_8$ aldehyde is benzaldehyde.

10. The method of claim 8 wherein said food item comprises post-harvest produce.

11. The method of claim 10 wherein the ester of a $C_2$-$C_5$ acid is selected from isoamyl acetate, isobutyl isobutyrate, and combinations thereof and wherein the $C_2$-$C_8$ aldehyde is benzaldehyde.

12. A method, comprising:

providing a composition comprising:

propanoic acid and at least one other component selected from isoamyl acetate, isobutyl isobutyrate, benzaldehyde and combinations thereof, wherein said composition is absent naphthalene and azulene derivative compounds;

wherein the ratio of propanoic acid to the at least one other component is 7:2; and contacting at least one of a microbe and a substrate with said composition, said composition in an amount sufficient to inhibit microbial growth.

13. The method of claim 12 wherein said substrate is a food item.

14. The method of claim 13 wherein said food item is selected from post-harvest fruits, nuts and vegetables.

* * * * *